United States Patent
Onuma

(10) Patent No.: US 10,070,925 B2
(45) Date of Patent: Sep. 11, 2018

(54) MEDICAL MANIPULATOR AND MEDICAL IMAGING SYSTEM INCLUDING MEDICAL MANIPULATOR

(71) Applicant: CANON KABUSHIKI KAISHA, Tokyo (JP)

(72) Inventor: Kazufumi Onuma, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 944 days.

(21) Appl. No.: 14/407,236

(22) PCT Filed: Jun. 5, 2013

(86) PCT No.: PCT/JP2013/003529
§ 371 (c)(1),
(2) Date: Dec. 11, 2014

(87) PCT Pub. No.: WO2013/187010
PCT Pub. Date: Dec. 19, 2013

(65) Prior Publication Data
US 2015/0182286 A1    Jul. 2, 2015

(30) Foreign Application Priority Data
Jun. 15, 2012  (JP) ................. 2012-135453

(51) Int. Cl.
*G05B 15/00* (2006.01)
*G05B 19/00* (2006.01)
(Continued)

(52) U.S. Cl.
CPC .......... *A61B 19/2203* (2013.01); *A61B 10/04* (2013.01); *A61B 17/00* (2013.01);
(Continued)

(58) Field of Classification Search
None
See application file for complete search history.

(56) References Cited

U.S. PATENT DOCUMENTS

| 4,924,852 A | 5/1990 | Suzuki |
| 2004/0111183 A1 | 6/2004 | Sutherland |

FOREIGN PATENT DOCUMENTS

| JP | 63-310379 A | 12/1988 |
| JP | H01-119601 A | 8/1989 |

(Continued)

OTHER PUBLICATIONS

Ed. by Helpful Pixie Bot (May 6, 2012), "Ultrasonic Motor", Retrieved from Wikipedia Jan. 21, 2016, https://en.wikipedia.org/w/index.php?title=Ultrasonic_motor&oldid=490949516.

(Continued)

*Primary Examiner* — Bhavesh V Amin
(74) *Attorney, Agent, or Firm* — Canon USA, Inc. I.P. Division

(57) ABSTRACT

A medical manipulator is improved in terms of invasiveness into a body tissue and an emergency avoidance difficulty. The medical manipulator includes a driving unit including a vibration-type actuator including a vibrating unit that generates a vibration wave, a moving unit movable relative to the vibrating unit in response to receiving the vibration wave, and a pressure application unit configured to apply a pressure between the vibrating unit and the moving unit. The medical manipulator further includes a manipulator unit connected to the driving unit and configured to be movable by being driven by the driving unit, a supporting unit that supports the driving unit and the manipulator unit, a driving circuit connected to the vibrating unit and configured to apply an AC voltage to the vibrating unit, and a torque control unit configured to control a holding torque with which the moving unit is held by the vibrating unit.

20 Claims, 14 Drawing Sheets

(51) Int. Cl.
*A61B 19/00* (2006.01)
*A61B 10/04* (2006.01)
*A61B 17/00* (2006.01)
*A61B 34/00* (2016.01)
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 34/73* (2016.02); *A61B 2010/045* (2013.01); *A61B 2017/00402* (2013.01); *A61B 2017/00539* (2013.01); *A61B 2017/00548* (2013.01); *A61B 2017/00862* (2013.01); *A61B 2034/2063* (2016.02); *A61B 2090/031* (2016.02); *A61B 2090/066* (2016.02); *A61B 2090/374* (2016.02); *A61B 2090/376* (2016.02)

(56) References Cited

FOREIGN PATENT DOCUMENTS

| | | |
|---|---|---|
| JP | 11-206152 A | 7/1999 |
| JP | 2003-265499 A | 9/2003 |
| JP | 2005163898 A | 6/2005 |
| JP | 2005-185072 A | 7/2005 |
| JP | 2006005975 A | 1/2006 |
| JP | 2010-524634 A | 7/2010 |
| WO | 2004/014244 A2 | 2/2004 |
| WO | 2008/134017 A1 | 11/2008 |
| WO | 2011057260 A2 | 5/2011 |

OTHER PUBLICATIONS

English translation of specification and claims of JP2005-185072.
English translation of specification and claims of JPS63-310379.
English translation of specification and claims of JPH11-206152.
English translation of specification and claims of JP2003-265499.
English translation of specification and claims of JP2006-005975.
English translation of specification and claims of JP2005-163898.

[Fig. 1A]
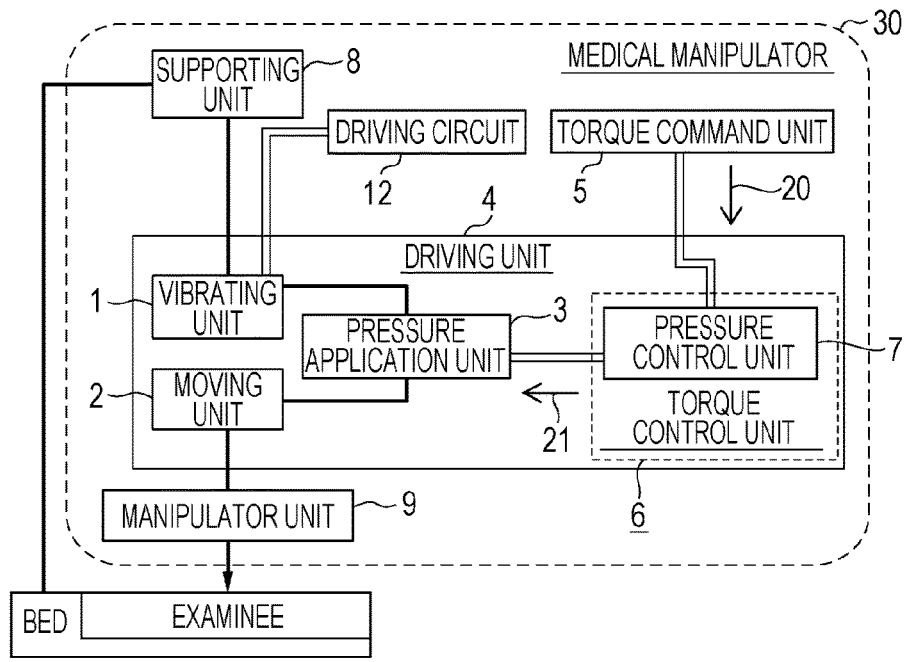
[Fig. 1B]
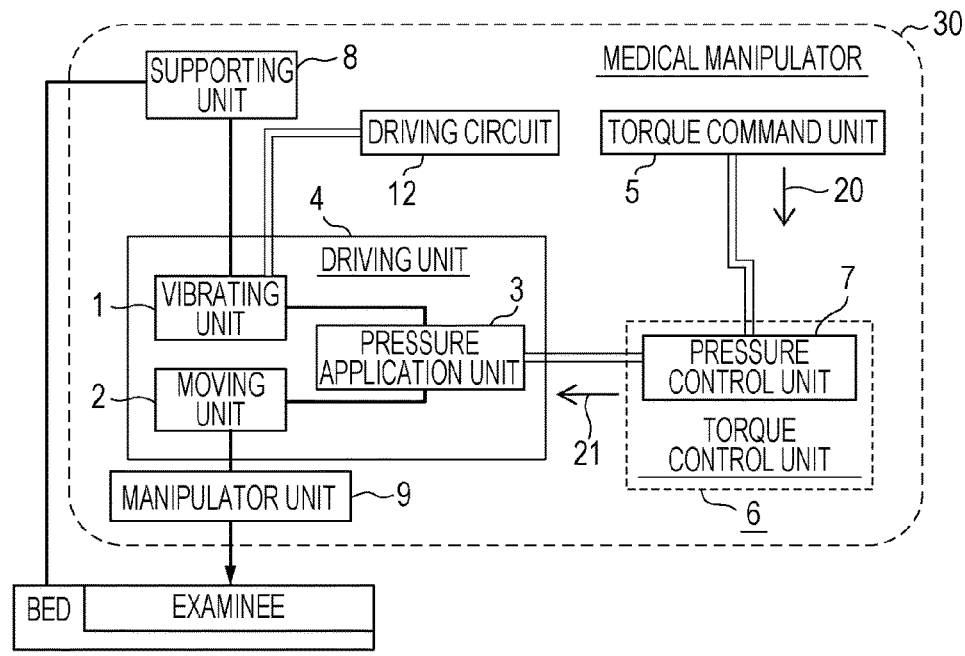

[Fig. 1C]
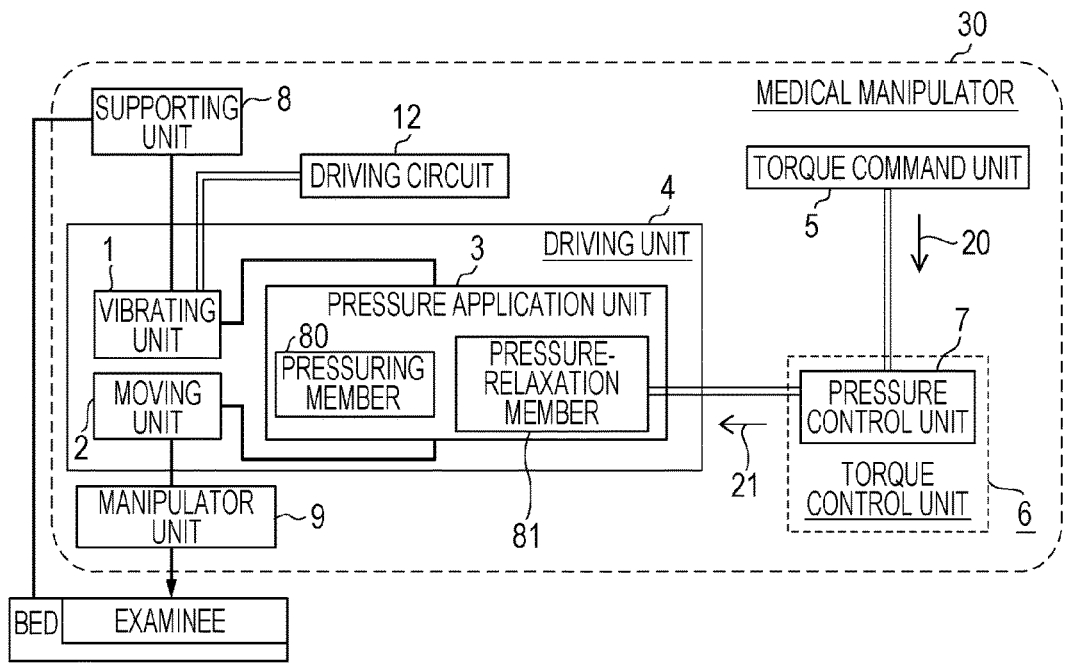
[Fig. 1D]
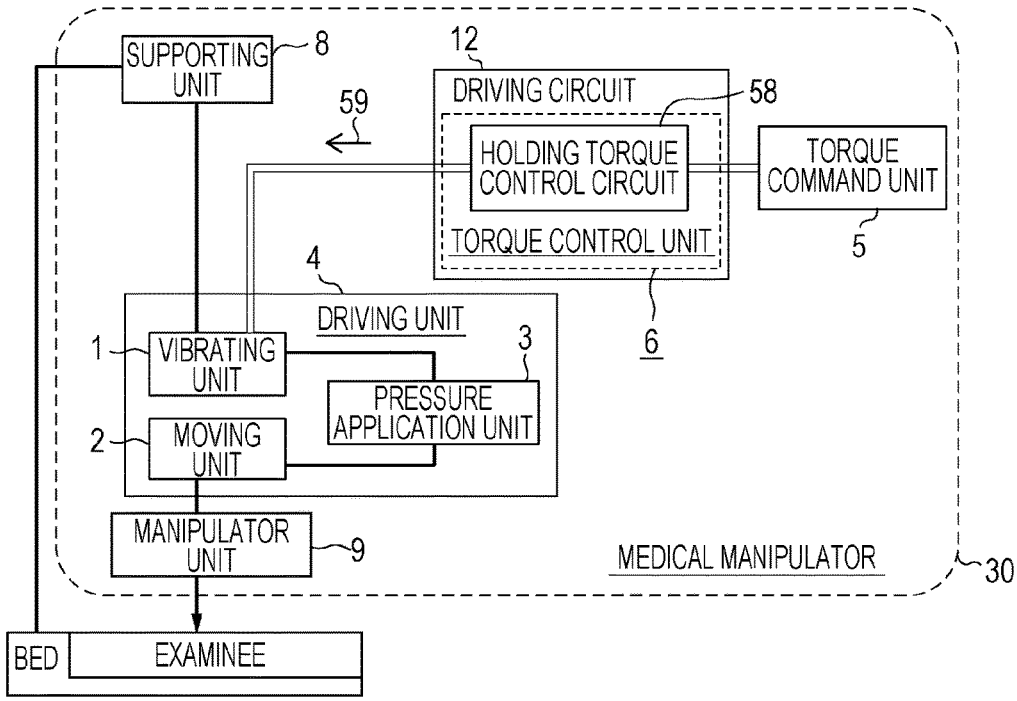

[Fig. 1E]
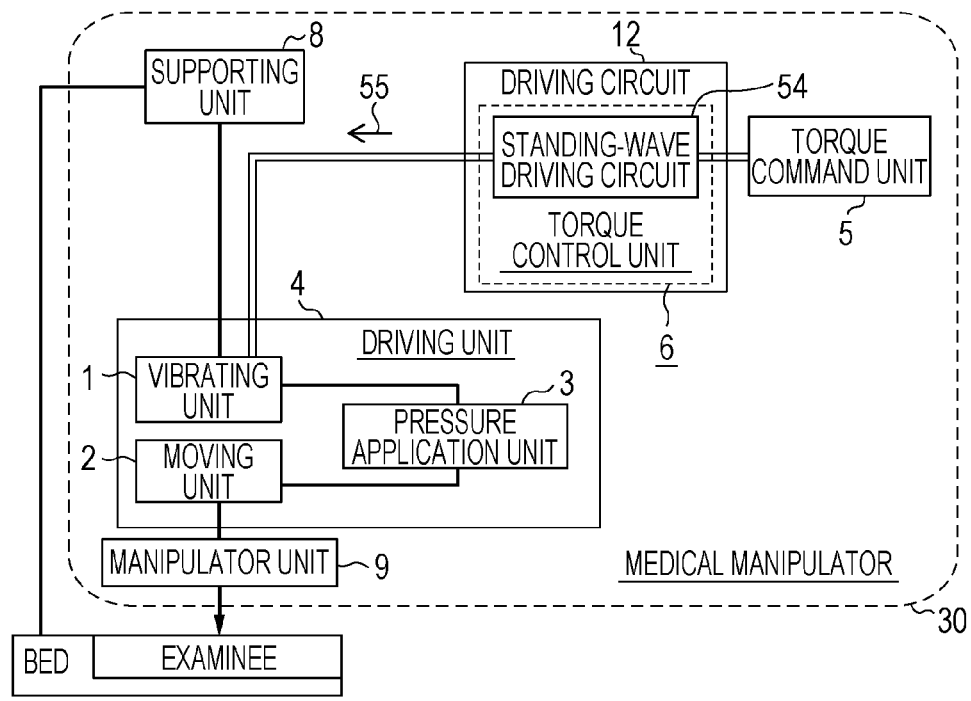
[Fig. 1F]
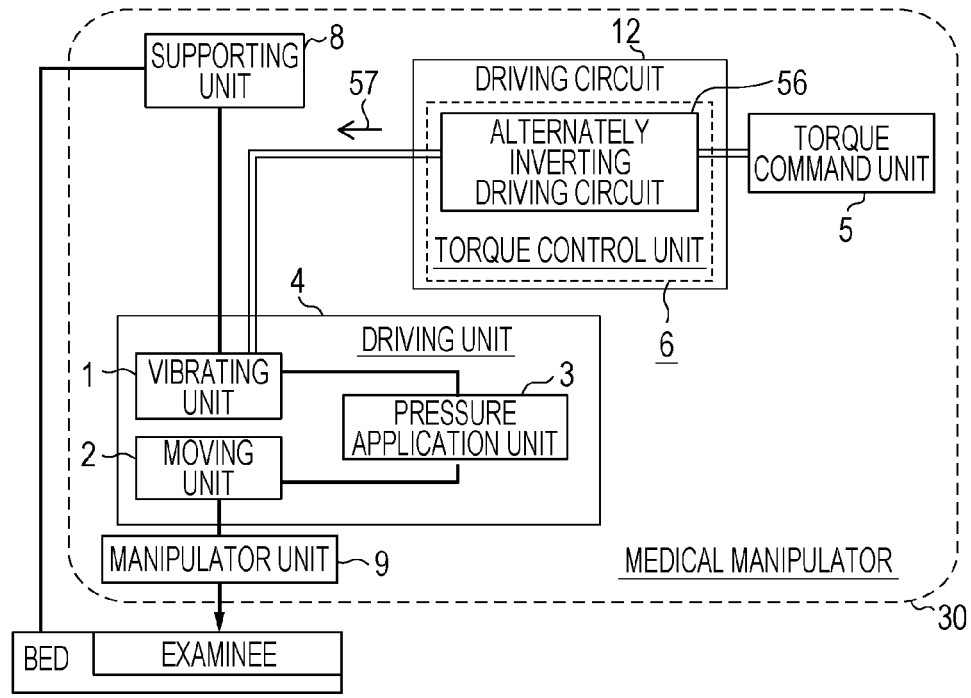

[Fig. 2A]
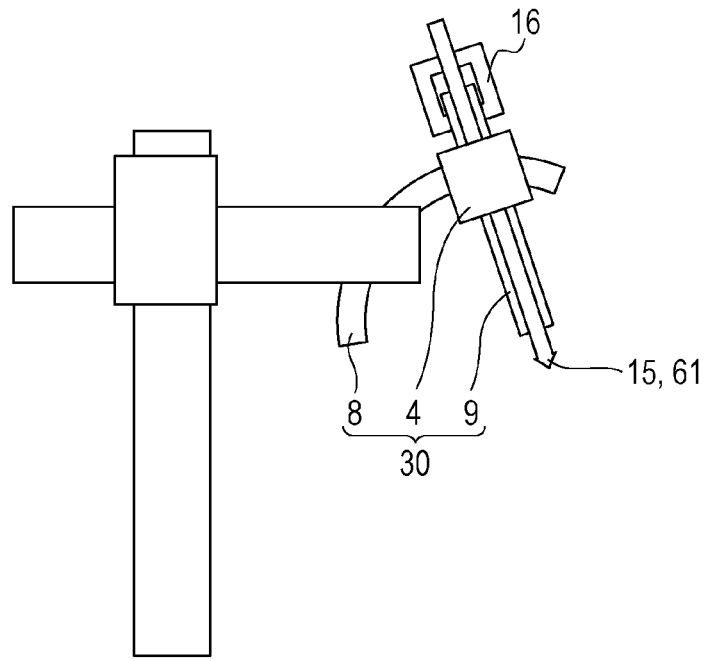
[Fig. 2B]
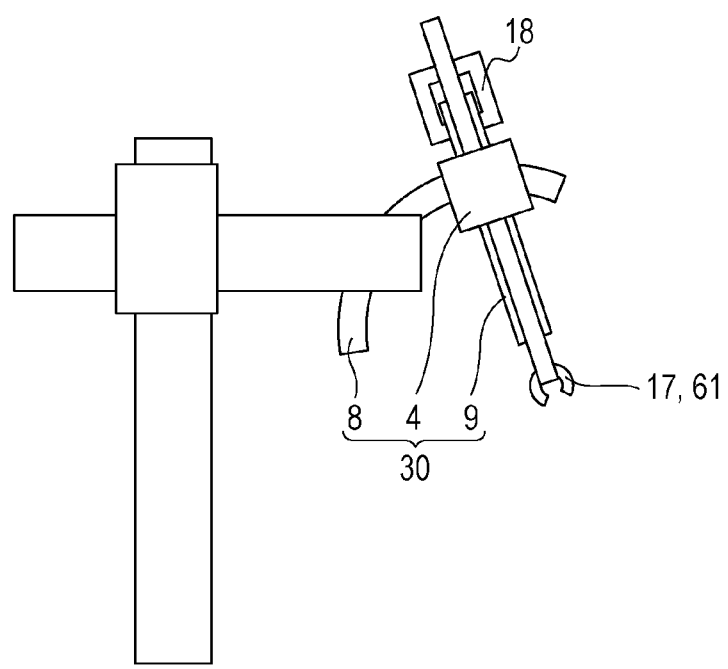

[Fig. 3A]
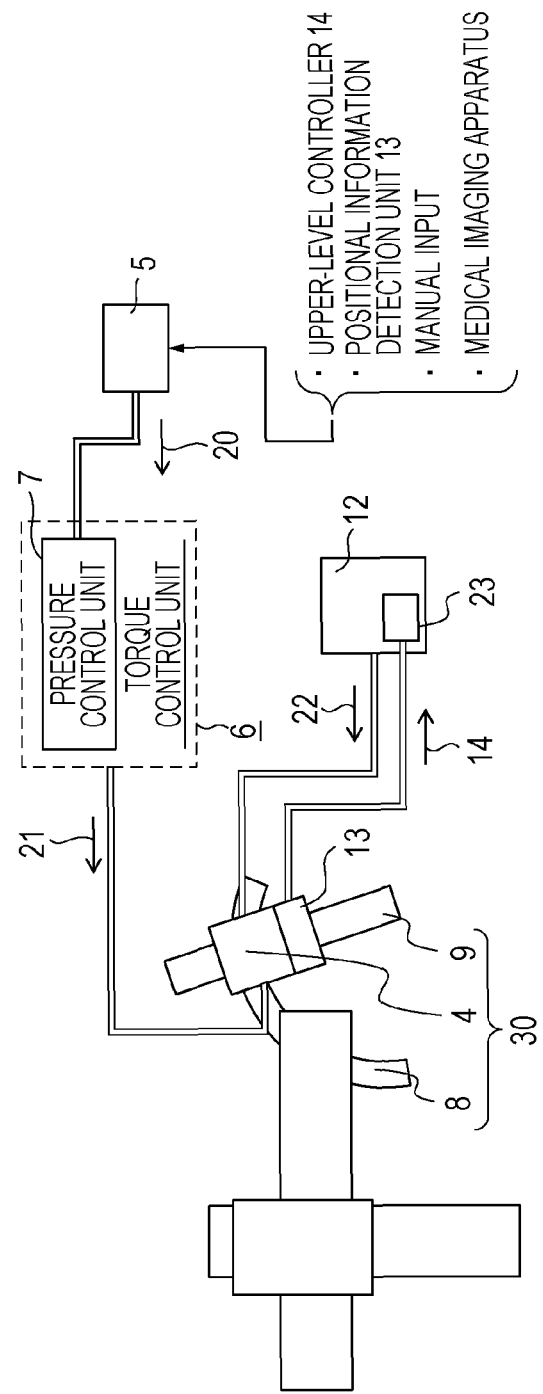

[Fig. 3B]
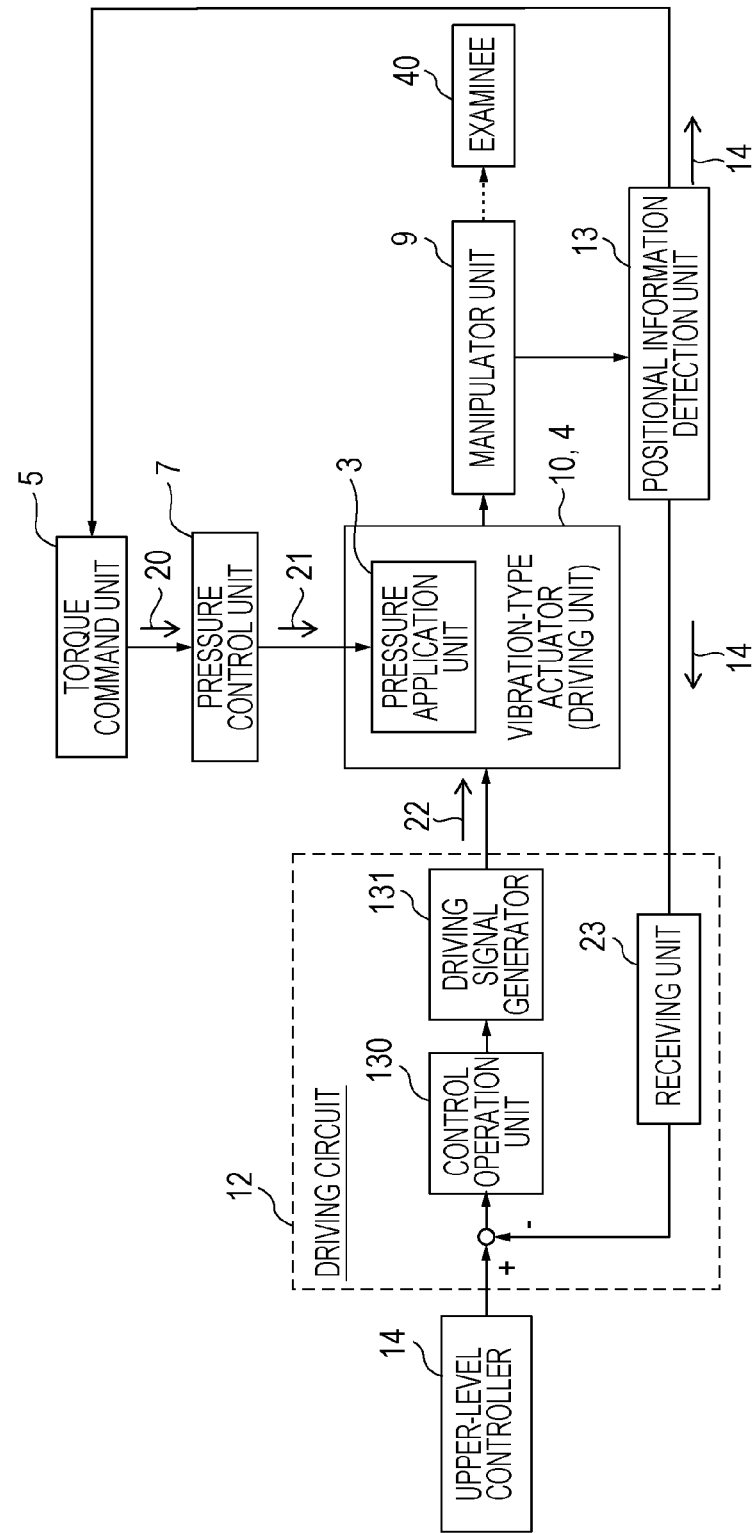

[Fig. 3C]
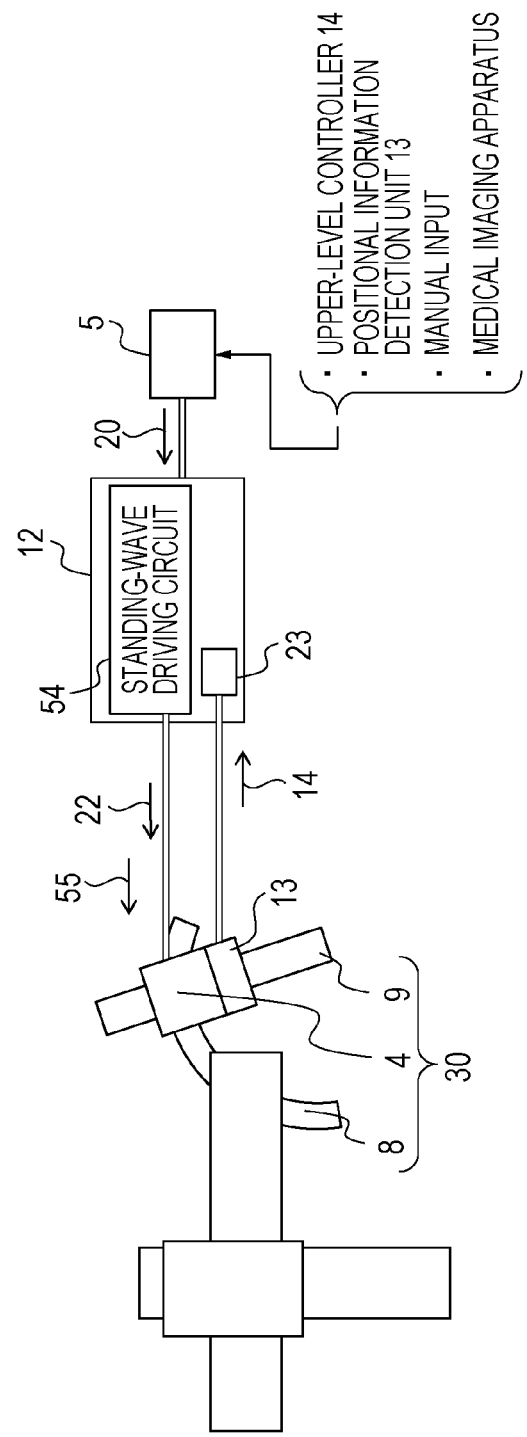

[Fig. 3D]
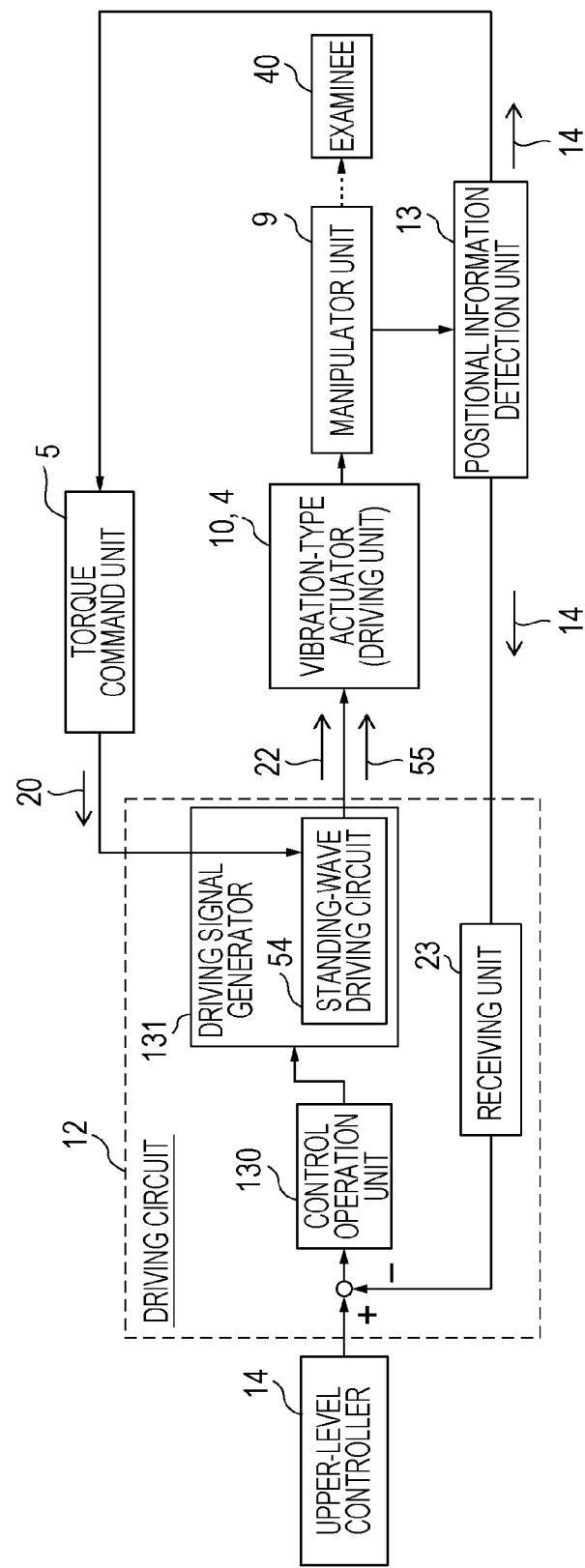

[Fig. 4A]
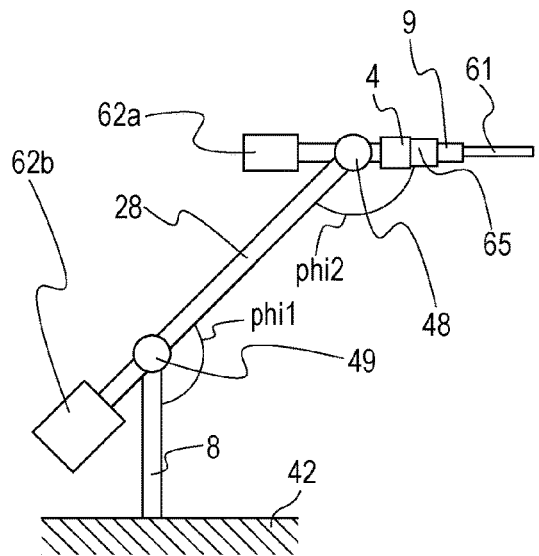
[Fig. 4B]
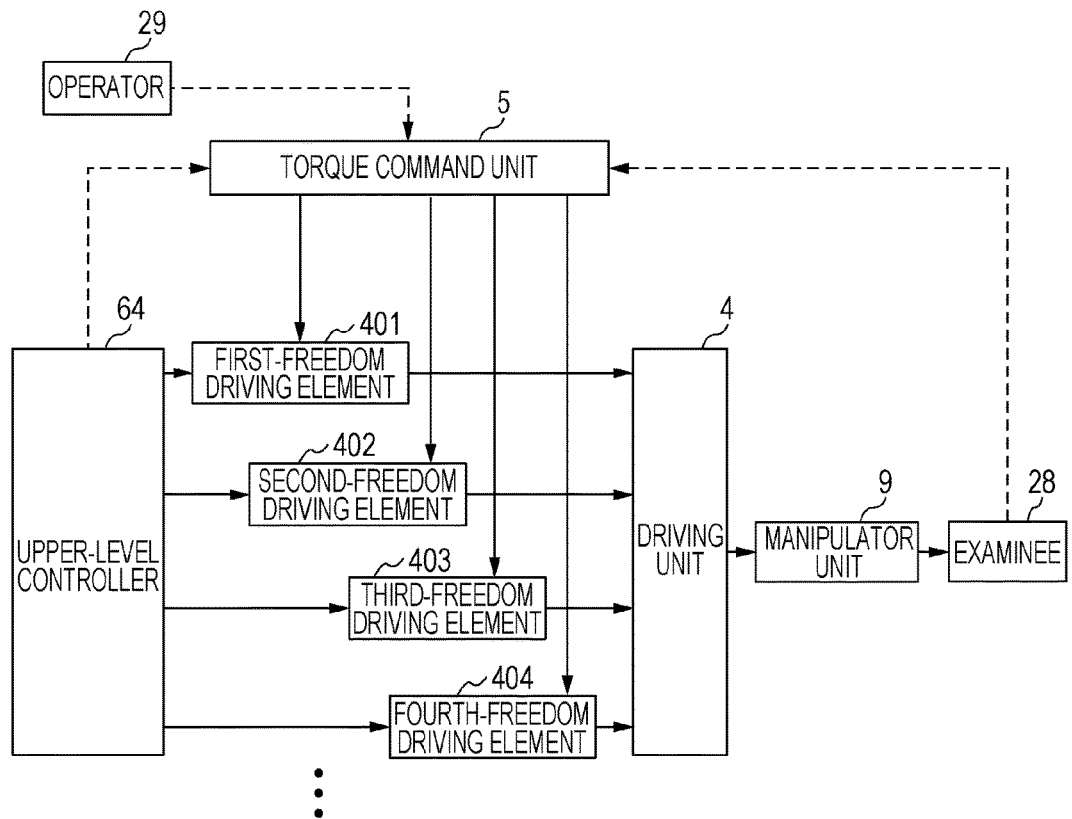

[Fig. 5]
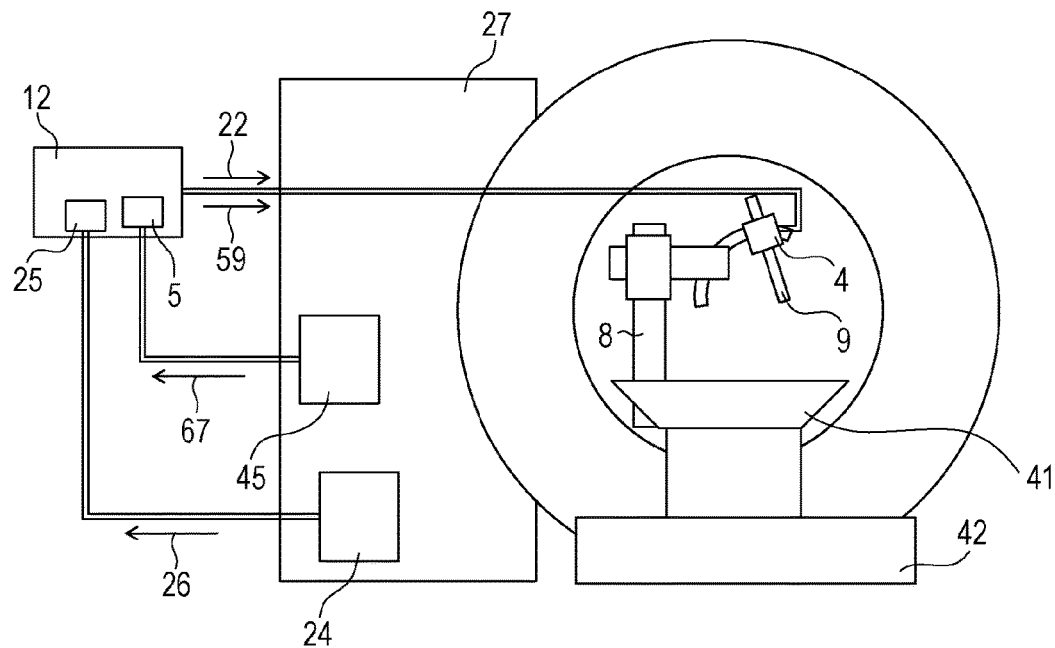
[Fig. 6A]
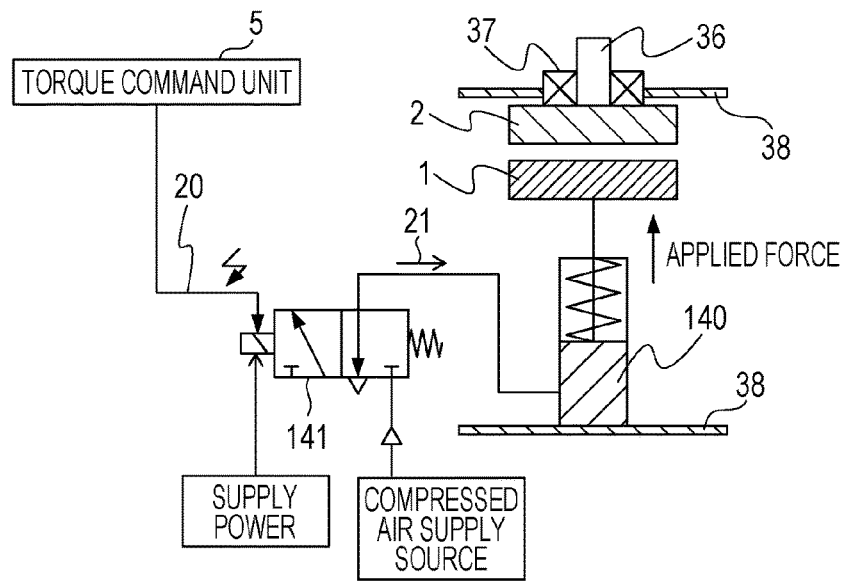

[Fig. 6B]
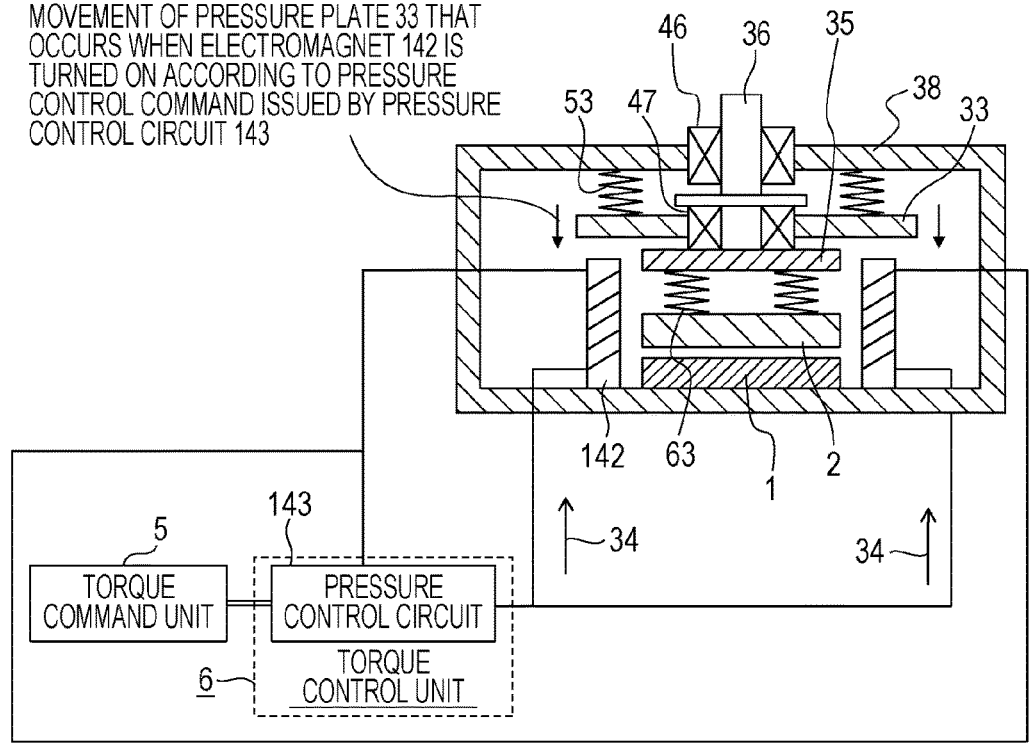
[Fig. 7A]
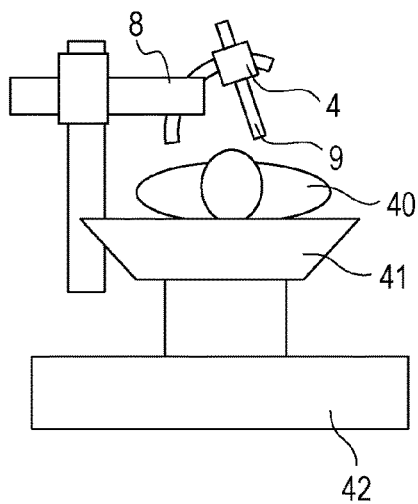

[Fig. 7B]
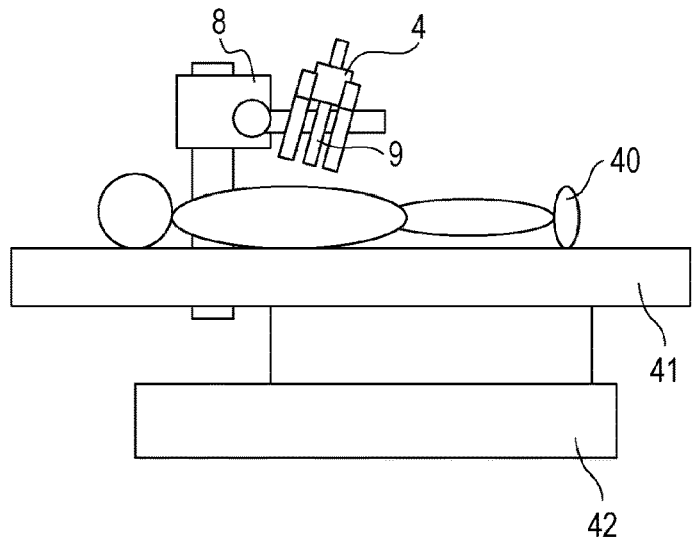
[Fig. 7C]
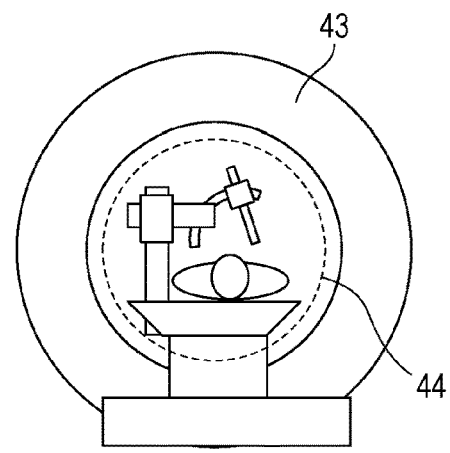
[Fig. 7D]
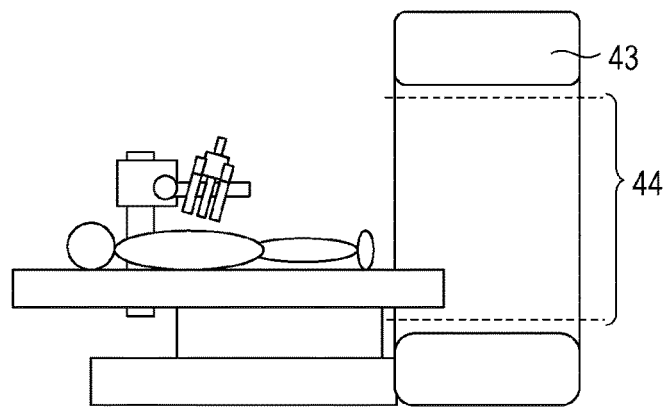

[Fig. 8]
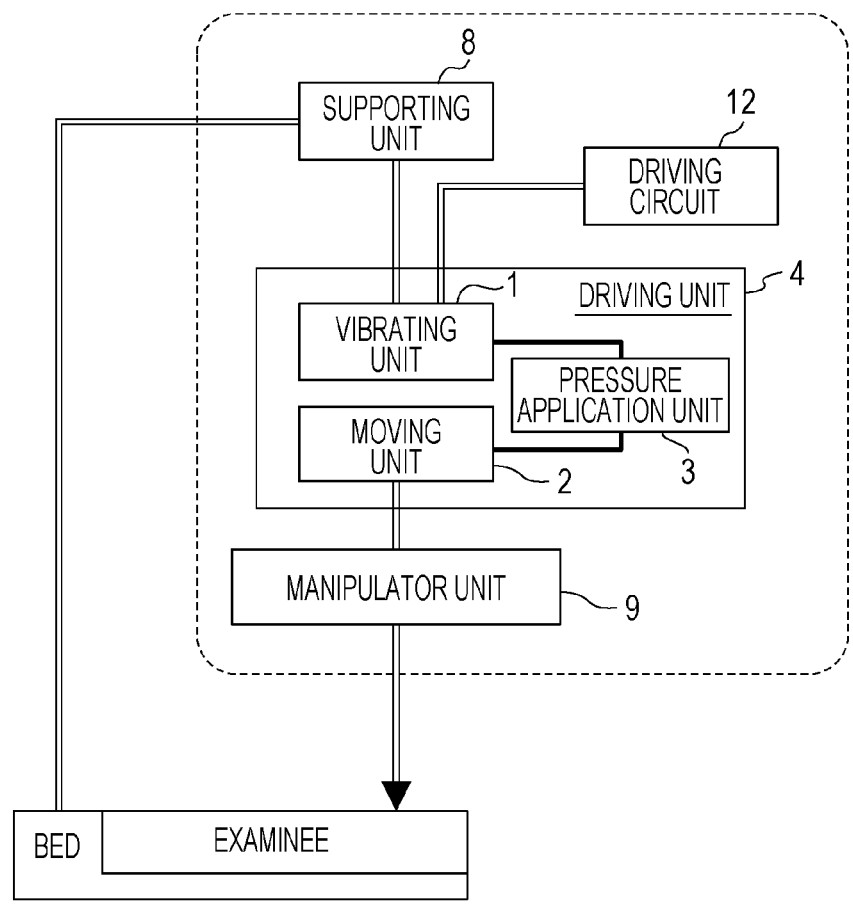

[Fig. 9]
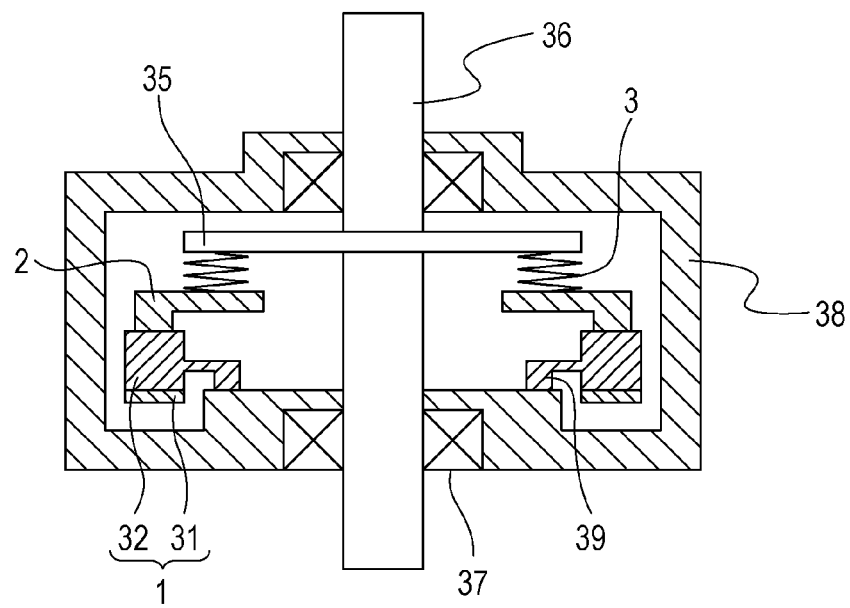

MEDICAL MANIPULATOR AND MEDICAL IMAGING SYSTEM INCLUDING MEDICAL MANIPULATOR

TECHNICAL FIELD

The present invention relates to a medical manipulator including a vibration-type actuator as a driving source and a medical imaging apparatus including a vibration-type actuator as a driving source.

BACKGROUND ART

Advancement in robotics technology leads to an increase in need for applications thereof to medical devices. A vibration-type actuator such as that illustrated in FIG. 9 is used as a driving source of a high-precision manipulator. The vibration-type actuator is capable of providing direct driving without using a speed reduction mechanism. Furthermore, the vibration-type actuator has a holding torque that allows the manipulator to keep its attitude even in a state in which no electric power is supplied. The features described above make the vibration-type actuator suitable for use in a medical manipulator with high-precision position controllability.

PTL 1 discloses a vibration-type actuator suitable for use with a magnetic resonance imaging (MRI) apparatus. The vibration-type actuator is formed in a tube structure including an inner tube and an outer tube, and a stator and a rotor serving as a driving source of a puncture apparatus are formed such that the stator and the rotor extend in a longitudinal direction of the tube structure and such that the stator and the rotor are disposed respectively on the inner tube and the outer tube so as to oppose each other. To solve a problem with a vibration of the medical manipulator caused by a bending vibration that occurs in the tube structure of the actuator, a groove and a thread are formed so as to extend spirally around the inner tube and the outer tube and so as to fit with each other. One of the stator and the rotor of the vibration-type actuator are disposed on one of the groove and the thread, and the other one of the stator and the rotor is disposed on the other one of the groove and the thread.

CITATION LIST

Patent Literature

PTL 1: Japanese Patent Laid-Open No. 2005-185072

SUMMARY OF INVENTION

Technical Problem

Because the vibration-type actuator has a holding torque, the supporting unit and the manipulator unit are locked against an external force when the medical manipulator is at rest. On the other hand, when an examinee is a living body, an autonomous and continuous displacement occurs in biological organs such as a respiratory organs, a circulatory organ, a digestive organ, a sense organ, a muscle tissue, and the like. It is difficult to either precisely predict displacements of the biological organs or suppress the displacements of the biological organs.

Therefore, a change in relative position between the medical manipulator and a biological organ in the living body causes the medical manipulator to receive an unbalanced load, which may cause a stress and strain to occur in various parts of the medical manipulator. The occurrence of the stress or strain may damage the medical manipulator, and thus it is desirable to improve reliability by solving the problems described above.

When an operator wants to manually operate the manipulator unit (by applying an external force) in a state in which the medical manipulator is in operation, the existence of the holding torque may make it difficult to selectively move only the manipulator unit, which may make it difficult to either install the medical manipulator at a correct position or adjust the position later.

As described above, when the medical manipulator having the vibration-type actuator serving as a driving source is used in the inside of an examinee, a problem may occur due to the holding torque of the vibration-type actuator.

Solution to Problem

A medical manipulator includes a driving unit including a vibration-type actuator including a vibrating unit configured to generate a vibration wave in response to being excited by an applied AC (alternating current) voltage, a moving unit configured to relatively move with respect to the vibrating unit in response to a reception of the vibration wave, and a pressure application unit configured to apply a pressure between the vibrating unit and the moving unit. The medical manipulator further includes a manipulator unit connected to the driving unit and configured to be movable by being driven by the driving unit, a supporting unit configured to support the driving unit and the manipulator unit, a driving circuit connected to the vibrating unit and configured to apply an AC voltage to the vibrating unit, and a torque control unit configured to control a holding torque with which the moving unit is held by the vibrating unit.

Advantageous Effects of Invention

The medical manipulator includes the vibration-type actuator capable of performing high-precision direct driving without using a speed reduction mechanism and capable of controlling the holding torque of the vibration-type actuator such that the high holding torque is reduced depending on a situation. These features of the vibration-type actuator provided in the medical manipulator make it possible to switch between a high-precision driving operation and a passive operation, which makes it possible to prevent the medical manipulator from being damaged by a movement of an object treated with the medical manipulator.

Furthermore, the features described above also make it possible to manually operate the manipulator by applying an external force thereto, which allows an increase in operability in terms of adjustment, positioning, or the like, when the medical manipulator is installed.

Further features of the present invention will become apparent from the following description of exemplary embodiments with reference to the attached drawings.

BRIEF DESCRIPTION OF DRAWINGS

FIG. 1A is a block diagram illustrating an example of a structure of a medical manipulator including a torque control unit according to an embodiment.

FIG. 1B is a block diagram illustrating an example of a structure of a medical manipulator including a torque control unit according to an embodiment.

FIG. 1C is a block diagram illustrating an example of a structure of a medical manipulator including a torque control unit according to an embodiment.

FIG. 1D is a block diagram illustrating an example of a structure of a medical manipulator including a torque control unit according to an embodiment.

FIG. 1E is a block diagram illustrating an example of a structure of a medical manipulator including a torque control unit according to an embodiment.

FIG. 1F is a block diagram illustrating an example of a structure of a medical manipulator including a torque control unit according to an embodiment.

FIG. 2A is a schematic diagram illustrating a medical procedure assist apparatus including a medical manipulator used as a medical puncture apparatus according to an embodiment.

FIG. 2B is a schematic diagram illustrating a medical procedure assist apparatus including a medical manipulator used as a medical biopsy apparatus according to an embodiment.

FIG. 3A is a schematic diagram illustrating an example of a manner in which a medical manipulator, a driving circuit, and a detection unit are connected to each other according to an embodiment.

FIG. 3B is a block diagram illustrating an example of a manner in which a medical manipulator, a driving circuit, and a detection unit are connected to each other according to an embodiment.

FIG. 3C is a schematic diagram illustrating an example of a manner in which a medical manipulator, a driving circuit, and a detection unit are connected to each other according to an embodiment.

FIG. 3D is a block diagram illustrating an example of a manner in which a medical manipulator, a driving circuit, and a detection unit are connected to each other according to an embodiment.

FIG. 4A is a schematic diagram illustrating a medical manipulator including a plurality of driving units according to an embodiment.

FIG. 4B is a block diagram illustrating a medical manipulator including a plurality of driving units according to an embodiment.

FIG. 5 is a schematic diagram illustrating a manner in which a medical manipulator according to an embodiment is connected to an external apparatus.

FIG. 6A is a schematic cross-sectional view illustrating an example of a structure of a vibration-type actuator including a pressure control unit according to an embodiment.

FIG. 6B is a schematic cross-sectional view illustrating an example of a structure of a vibration-type actuator including a pressure control unit according to an embodiment.

FIG. 7A is a diagrams illustrating a connection between a medical manipulator according to an embodiment and an examinee or a medical imaging apparatus.

FIG. 7B is a diagrams illustrating a connection between a medical manipulator according to an embodiment and an examinee or a medical imaging apparatus.

FIG. 7C is a diagrams illustrating a connection between a medical manipulator according to an embodiment and an examinee or a medical imaging apparatus.

FIG. 7D is a diagrams illustrating a connection between a medical manipulator according to an embodiment and an examinee or a medical imaging apparatus.

FIG. 8 is a block diagram illustrating a structure of a medical manipulator including a vibration-type actuator.

FIG. 9 is a schematic cross-sectional view illustrating an example of a structure of a vibration-type actuator according to an embodiment.

DESCRIPTION OF EMBODIMENTS

First, with reference to FIG. 9, a description is given below as to a basic structure of a vibration-type actuator 10 applicable to a medical manipulator according to an embodiment. FIG. 9 is a schematic cross-sectional view illustrating a structure of a ring-shape vibration-type actuator. In FIG. 9, for simplicity, a torque control unit is not illustrated.

A ring-shape piezoelectric element 31 is bonded to a ring-shape vibrator 32. The piezoelectric element 31 generates a vibration in response to being excited by an applied electric signal. As for such an electric signal applied to the piezoelectric element 31, for example, an AC voltage signal may be employed. The vibrator 32 amplifies the vibration generated by the piezoelectric element 31 into the form of a deflection vibration. A pressure application unit 3 applies a pressure between the moving unit 2 and the vibrator 32. The vibration of the vibrator 32 is transmitted to the moving unit 2 by a frictional force. As a result, the moving unit 2 rotates. The moving unit 2 and the torque transmission member 35 are connected via the pressure application unit 3 such that the rotation of the moving unit 2 causes an output shaft 36 to rotate. The output shaft 36 is connected rotatably to a housing 38 via a bearing 37. On the other hand, the vibrator 32 is connected firmly to the housing 38 via a connecting element 39. Hereinafter, a structure including the vibrator 32 and the piezoelectric element 31 will be referred to as a vibrating unit 1.

Although in the example of the vibration-type actuator applicable to the medical manipulator according to the embodiment illustrated in FIG. 9, the vibration-type actuator is of the ring type in which the vibrating unit 1 and the moving unit 2 are disposed in the form of a ring around a rotation shaft 36, the structure of the vibration-type actuator is not limited to that of this example. For example, the vibration-type actuator may be formed of a straight line type in which the vibrating unit 1 and the moving unit 2 are disposed in a straight line, or may be formed of a tube type including an inner tube and an outer tube in one of which one of the vibrating unit 1 and the moving unit 2 is disposed and in the other one of which the other one of the vibrating unit 1 and the moving unit 2 is disposed.

The pressure application unit 3 is configured to provide a pressure in an axial direction along the rotation shaft 36, but the pressure application unit 3 does not have a change in form in a direction of rotation. For example, a belleville spring or the like may be used as the pressure application unit 3. The pressure in the axial direction given by the pressure application unit 3 allows the vibration-type actuator to have a holding torque, which is a feature greatly different from that of an electromagnetic motor that provides a driving force by a Lorentz force. Another feature of the vibration-type actuator is that it is capable of providing a large torque at a low speed compared with the electromagnetic motor. The features described above make it possible to easily realize a direct drive mechanism using no speed reduction mechanism. Thus, the vibration-type actuator according to embodiments may be used to achieve a direct drive operation.

In the medical manipulator including the vibration-type actuator according to embodiments, it is possible to control a holding torque between a supporting unit 8 and a manipulator unit 9 to an optimum value so as to avoid the above-described problem caused by the holding torque of the vibration-type actuator.

Next, referring to FIGS. 1A to 1F, a basic structure of the medical manipulator is described below. As illustrated in FIGS. 1A to 1F, the medical manipulator 30 according to the embodiment includes a driving unit 4 including at least a vibration-type actuator 10 including a vibrating unit 1 configured to generate a vibration wave in response to being excited by an applied AC voltage, a moving unit 2 configured to relatively move with respect to the vibrating unit 1 in response to a reception of the vibration wave, and a pressure application unit 3 configured to apply a pressure between the vibrating unit 1 and the moving unit 2. The medical manipulator 30 further includes a supporting unit 8 that supports the driving unit 4, a manipulator unit 9 supported by the driving unit 4, a driving circuit 12 connected to the vibrating unit 1 and configured to apply an AC voltage to the vibrating unit 1, and a torque control unit 6 configured to control a holding torque of the driving unit 4.

The vibration-type actuator 10 is used as a constituent part of the driving unit 4 such that either one of the vibrating unit 1 and the moving unit 2 in the driving unit 4 is supported by the supporting unit 8, and the other one of the vibrating unit 1 and the moving unit 2 supports the manipulator unit 9, thereby allowing the driving force of the vibration-type actuator 10 to be used as a torque that drives the medical manipulator 30 in a manipulating operation.

The driving unit 4 includes at least the vibration-type actuator 10 serving as a driving source to relatively move the manipulator unit 9 with respect to the supporting unit 8, and the driving unit 4 may further include a mechanical transmission unit, an electro-magnetic clutch, and the like. That is, in the medical manipulator according to the embodiment, the vibration-type actuator 10 is one of constituent parts forming the driving unit 4.

In the embodiment, the provision of the torque control unit 6 in the medical manipulator 30 makes it possible to control the holding torque between the vibrating unit 1 and the moving unit 2 from the outside of the medical manipulator at a proper timing. A mechanism of variably controlling the holding torque from the outside will be described later with reference to specific examples.

The medical manipulator may be embodied into two forms depending on the structure of the torque control unit 6 and the connection of the torque control unit 6.

More specifically, in the medical manipulator according to a first embodiment, a pressure control unit 7 connected to the pressure application unit 3 is used as the torque control unit 6. FIGS. 1A, 1B, and 1C are schematic diagrams illustrating examples of structures according to the first embodiment. On the other hand, in the medical manipulator according to a second embodiment, the torque control unit 6 is configured such that the driving circuit 12 connected to the vibrating unit 1 includes a holding torque control circuit 58. FIGS. 1D, 1E, and 1F are schematic diagrams illustrating examples of structures according to the second embodiment.

First Embodiment

Referring to schematic diagrams illustrated in FIGS. 1A, 1B, and 1C, the first embodiment is described below.

In each of the examples illustrated in FIGS. 1A, 1B, and 1C, the pressure control unit 7 serving as the torque control unit 6 is connected to the pressure application unit 3 provided in the driving unit 4. In the structures illustrated in FIG. 1A and FIG. 1B, the pressure applied between the vibrating unit 1 and moving unit 2 by the pressure application unit 3 is controllable according to a torque control signal 21 output from the pressure control unit 7. The structure illustrated in FIG. 1C is a modification to the first embodiment, that is, the pressure application unit 3 includes a pressuring member 80 configured to apply a constant pressure to the moving unit 2 with respect to the vibrating unit 1, a pressure reduction unit 81 configured to provide a pressure in a direction opposite to the direction of the pressure applied by the pressuring member 80, and a pressure control unit 7 connected to the pressure reduction unit 81. In the first embodiment, as illustrated in FIG. 1A and FIG. 1B, the torque control unit 6, that is, the pressure control unit 7 may be disposed in the inside of the driving unit 4 or may be disposed in the outside of the driving unit 4.

Referring to FIG. 6A, an example of a structure of a vibration-type actuator according to the first embodiment is described below. In this structure, a pneumatic cylinder 140 and a control valve 141 are respectively used as the pressure application unit 3 and the pressure control unit 7.

The example of the structure illustrated in FIG. 6A corresponds to the structure illustrated in FIG. 1A or FIG. 1B. In the structure of the vibration-type actuator illustrated in FIG. 6A, the moving unit 2 connected to the rotation shaft 36 is rotatably connected to the housing 38 via the bearing 37. Furthermore, the vibrating unit 1 is connected one end of a piston of the pneumatic cylinder 140 and thus the vibrating unit 1 is connected to the housing 38 via the pneumatic cylinder 140. This structure allows the vibrating unit 1 to move in both directions toward and away from the moving unit 2. The pneumatic cylinder 140 is connected to a pneumatic output of the control valve 141 via a plastic tube such that the pressure applied between the moving unit 2 and the vibrating unit 1 is remotely controllable by controlling the pressure of the compressed air supplied from the control valve 141. An electromagnetic valve 141 for controlling the pneumatic pressure may be used by way of example as the control valve 141.

Next, a description is given below as to a mechanism of controlling the holding torque in the medical manipulator including the vibration-type actuator configured as illustrated in FIG. 6A. When the torque command unit 5 is outputting a torque control command 20 to the control valve 141, the control valve 141 outputs a compressed air supplied from the compressed air supply source as a pressure control signal 21 to the pneumatic cylinder 140. The piston of the pneumatic cylinder 140 urges the vibrating unit 1 in a direction toward the moving unit 2. As a result, a particular pressure is applied between the vibrating unit 1 and the moving unit 2 and a holding torque occurs between the vibrating unit 1 and the moving unit 2.

On the other hand, during a period in which no torque control command 20 is applied from the torque command unit 5 to the control valve 141, the control valve 141 discharge the air in the inside of the pneumatic cylinder 140 to the atmosphere. This results in a reduction in pressure between the vibrating unit 1 and the moving unit 2, and thus a reduction in holding torque between the vibrating unit 1 and the moving unit 2.

In the structure illustrated in FIG. 6A, the pneumatic cylinder 140 supplies a pressure to the vibrating unit 1. However, the structure is not limited to this example. For example, the pressure may be applied to the moving unit 2, or the pressure applied to the vibrating unit 1 may be given via another element.

In the example illustrated in FIG. 6A, the pneumatic cylinder 140 is used as the pressure application unit 3, and the electromagnetic valve serving as the control valve 141 is used as the pressure control unit 7. However, the embodiment is not limited to this example, and another type of pressure control unit or another type of pressure application unit may be used.

Another example of the pressure control unit is a control valve configured to be capable of controlling the flow rate of a compressed gas an incompressible liquid. Another example of the pressure application unit is a gas pressure cylinder or a hydraulic cylinder. For example, the pneumatic cylinder 140 may be replaced with another gas pressure control unit using a dry nitrogen gas or the like as a medium. The pressure control unit, the pressure control signal, and the pressure application unit may be combined in various manners as long as the combination is capable of controlling the pressure. For example, a combination of a hydraulic cylinder, a hydraulic pressure signal, and a hydraulic control apparatus may be employed as an alternative. In a case, as in the present embodiment, where the pneumatic cylinder 140 and the electro-magnetic valve 141 for controlling the pneumatic pressure are used, a medium reflux system is not necessary unlike the hydraulic control system. That is, it is allowed to discharge a compressed air into the ambient, which makes it possible to achieve the system with a small size, and makes it unnecessary to be concerned with degradation of the medium.

Next, referring to FIG. 6B, another example of a structure of the vibration-type actuator according to the first embodiment is described below. In this example, the torque control unit 6 uses an electromagnetic force. FIG. 6B illustrates the example of the structure of the vibration-type actuator according to the first embodiment in which the pressure application unit 3 includes an electromagnet 142, a moving-unit-side elastic element 63, and a pressure plate 33, and a pressure control circuit 143 is used as the pressure control unit 7. The example of the structure illustrated in FIG. 6B corresponds to the structure illustrated in FIG. 1A or FIG. 1B.

The pressure control signal 21 illustrated in FIG. 1A or FIG. 1B corresponds to a DC (direct current) current 34 output from the pressure control circuit 143 illustrated in FIG. 6B and flowing through the electromagnet 142.

An example of a pressure application mechanism configured to control the vibration-type actuator according to the present embodiment is described below. The vibrating unit 1 is fixed to one end of the housing 38. The moving unit 2 is connected to the other end of the housing 38 via a moving-unit-side elastic element 63, the rotation shaft 36, two bearings, a pressure plate 33 formed of a magnetic material, and a housing-side elastic element 53. The length and the elastic constant of the housing-side elastic element 53 are set so as to satisfy conditions described below, and the housing-side elastic element 53 is connected to the housing 38 and the pressure plate 33. A first condition is that when no current is supplied to the coil of the electromagnet 142, no elastic deformation occurs, and the pressure plate 33 and the electromagnet 142 are separated apart from each other. A second condition is that when a current equal to or greater than a predetermined value is input to the coil of the electromagnet 142, the pressure plate 33 is brought into contact with the electromagnet 142. The length and the elastic constant of the moving-unit-side elastic element 63 are set so as to satisfy conditions described below, and the moving-unit-side elastic element 63 is connected to the pressure plate 33 and the moving unit 2. A first condition is that when no current is supplied to the coil of the electromagnet 142, no elastic deformation occurs, and the moving unit 2 and the vibrating unit 1 are separated apart from each other. A second condition is that when a current equal to or greater than a predetermined value is input to the electromagnet 142, the pressure plate 33 moves and the movement of the pressure plate 33 causes the moving unit 2 to come into contact with the vibrating unit 1 and be urged against the vibrating unit 1 by a particular pressure.

In the present embodiment, the bearing has a composite structure including a bearing 46 freely movable in a direction along the rotation shaft 36 and a bearing 47 freely movable only in a direction of rotation. Note that the structure of the bearing is not limited to that described above. In a case where the first condition in terms of the separation does not need to be satisfied, the bearing 46 may be replaced with a bearing configured to be movable only in the direction of rotation.

The operation of vibration-type actuator illustrated in FIG. 6B is described in more detail below. When a DC current serving as the pressure control signal 21 output from the electromagnet control circuit serving as the pressure control circuit 143 is passed through the coil of the electromagnet 142, the electromagnet 142 generates a magnetic force. The magnetic force causes the pressure plate 33 connected to the moving unit 2 to be urged in a direction toward the vibrating unit 1. As a result, the moving unit 2 and the vibrating unit 1 are urged against each other. Note that when the coil of the electromagnet 142 is in an off-state, the gap between the electromagnet 142 and the pressure plate 33 is set to be greater than the gap between the moving unit 2 and the vibrating unit 1 such that the pressure applied between the vibrating unit 1 and the moving unit 2 may be continuously controlled by controlling the magnitude of the current flowing through the coil. Alternatively, a driving mechanism using an oil or water hydraulic pressure, or a mechanism using no power may be used to change the applied pressure, although further detailed structures thereof are not described. Note that the applied pressure varying unit is not limited to those described above, but the applied pressure varying unit may be configured in various manners as long as it is possible to dynamically change the pressure applied between the vibrating unit 1 and the moving unit 2.

In the structure illustrated in FIG. 6B, if the housing-side elastic element 53 is removed and the electromagnet 142 is moved to the original location of the removed housing-side elastic element 53 and the electromagnet 142 is fixed to the housing 38, then a structure according to the first embodiment illustrated in FIG. 1C is obtained. In this structure, the pressure application unit 3 is configured so as to include the pressure reduction unit 81 including the pressure plate 33 and the electromagnet 142, and the pressuring member 80 including the moving-unit-side elastic element 63. The pressure control unit 7 corresponds to the pressure control circuit 143.

Next, a mechanism of controlling the holding torque by the pressure control unit is described below. The holding torque is substantially proportional to the magnitude of the applied pressure. Therefore, it is possible to control the holding torque by varying the pressure applied between the vibrating unit and the moving unit depending on the desired holding torque. For example, when it is desired to achieve passivity while having resistance against a particular external force, the holding torque may be reduced by setting the pressure applied between the vibrating unit and the moving unit, not to zero, but to a value smaller than a standard value used in driving the actuator in a forward or reverse direction.

More specifically, the applied pressure may be set to a value in a range of ¹⁄₁₀₀ to ½ of the standard value. More preferably, the applied pressure may be set to a value in a range of ¹⁄₅₀ to ⅕ of the standard value such that it is ensured to reduce the risk that the manipulator is damaged when the manipulator unit is placed in a particular region of the inside of an examinee.

The reduction in pressure applied between the vibrating unit and the moving unit results in a reduction in holding torque of the vibration-type actuator, which may make it difficult for the supporting unit to support the manipulator unit. This may make it difficult to keep the attitude of the whole manipulator. For example, in a case where a plurality of vibration-type actuators are disposed in a multiple-joint mechanism so as to achieve a plurality of degrees of control freedom, a large number of joints or degrees of freedom may further increase a difficulty of keeping the attitude. To avoid the above situation, a counter weight 62 may be provided as a compensation unit as illustrated in FIG. 4A. FIG. 4A illustrates an example of a structure in which a plurality of vibration-type actuators are serially connected to achieve a multiple-joint mechanism. The structure illustrated in FIG. 4A includes a procedure assist device driving unit 65 configured to drive a procedure assist device 61 in a moving direction, a driving unit 4 configured to drive a manipulator unit 9 in a uniaxial direction, a rotation driving unit 48 configured to control an angle phi2 with respect to an intermediate manipulator unit 28 of the manipulator unit 9, and a rotation driving unit 49 configured to control an angle phi1 with respect to a supporting unit 8 of the intermediate manipulator unit 28, thereby achieving four degrees of freedom. A moment occurs about the driving unit 48 due to gravitational forces acting on the driving unit 4 driven by the rotation driving unit 48, the driving unit 65, the manipulator unit 9, and the procedure assist device 61, and other elements (not illustrated in the figure) that connect the units described above to the driving unit 48. To compensate for the moment due to the gravitational forces, a first counterweight 62a is disposed on an end of the supporting unit opposing the manipulator unit via the driving unit that reduces the holding torque. Similarly, a second counterweight 62b is disposed to compensate for a moment that occurs about the driving unit 49 due to a gravitational force acting on the intermediate manipulator unit 28 and other elements connected to the intermediate manipulator unit 28. The provision of the counterweights 62a and 62b makes it possible for the medical manipulator to have high passivity of the manipulator unit 9 while minimizing fluctuation of the attitude of the overall manipulator in a low-holding-torque operation mode.

As illustrated in FIG. 4A, the medical manipulator including a plurality of driving units according to the present embodiment may be configured such that a plurality of driving units are disposed at proper locations on a path from a supporting unit to a manipulator unit located at the farthest position from the supporting unit such that the respective driving units are allowed to drive the manipulator unit in different directions. This structure makes it possible to uniquely control the position of the manipulator unit, which allows an expansion of a controllable region and an increase in control precision.

Next, referring to FIG. 3A and FIG. 3B, a mechanism of an operation based on the torque command unit 5 in the medical manipulator according to the first embodiment is described below. FIG. 3A is a schematic diagram illustrating a structure obtained by adding a position information detection unit 13 to the structure of the medical manipulator 30 according to the first embodiment illustrated in FIGS. 1A to 1C. FIG. 3B is a block diagram illustrating details of signal flows in the structure illustrated in FIG. 3A.

An example of a process is described below in which the operation mode of the medical manipulator according to the first embodiment is changed based on a command issued by the torque command unit 5. In the medical procedure assist apparatus including the procedure assist device, the holding torque is controlled by the torque command unit during a procedure assist action in a manner as described below. To provide a better understanding of the operation of manipulator unit 9, the procedure assist device is not illustrated in FIG. 3A and FIG. 3B.

First, a description is given below as to an operation mode employed, at a stage of inserting the manipulator unit 9 into the inside of an examinee, to precisely put the procedure assist device at a desired position in the inside of the examinee. At this stage, as illustrated in FIG. 3B, based on a position information signal 14 serving as a detection signal transmitted from the position information detection unit 13, the torque command unit 5 determines that a target position has not yet been reached, and thus the torque command unit 5 sends a torque control command 20 to the pressure control unit 7 to increase the applied pressure. In response, the pressure control unit 7 outputs a pressure control signal 21 to the pressure application unit 3 of the driving unit 4 to adjust the applied pressure to a specified value. As a result, the specified pressure is applied between the vibrating unit and the moving unit, and the manipulator unit 9 is supported with respect to the supporting unit 8 by a particular holding torque. Thus, the manipulator unit 9 is moved by the operation torque of the driving unit 4 to the target point until the procedure assist device reaches the target point.

Next, a description is given below as to an operation at a stage after the manipulator has reached the target point. It is necessary to maintain the procedure assist device in the inside of the examinee during a period in which a procedure is performed using the living body procedure assist device. In the present embodiment, a determination as to whether the manipulator unit 9 has reached the target position is made based on the position information signal 14 transmitted from the position information detection unit 13 to the torque command unit 5. If it is determined that the manipulator unit 9 has reached the target position, the torque command unit 5 transmits a torque control command 20 to the pressure control unit 7 to reduce the applied pressure. As a result of a sequence of operations detection→position information transmission→judgment→command transmission, the holding torque of the vibration-type actuator of the driving unit 4 is reduced, and thus the holding torque of the manipulator unit 9 with respect to the supporting unit 8 illustrated in FIG. 3A is also reduced. As a result, the procedure assist device and the manipulator unit 9 inserted in the inside of the examinee are not fixed with respect to the on-apparatus reference but they move following the movement of the examinee 40. As described above, in the present embodiment, the medical manipulator operates according to the position information of the manipulator such that the manipulator is prevented from being damaged.

Next, an operation mode of the manipulator after the end of the procedure period is described below. To pull the procedure assist device out of the examinee 40, the torque command unit 5 issues a torque control command 20 to the pressure control unit 7 to generate an applied pressure. This makes it possible for the manipulator, as in the inserting operation, to pull the procedure assist device and the manipulator unit out of the inside of the examinee 40 while maintaining a particular holding torque.

A trigger that causes the torque command unit 5 to issue a command transmission to the pressure control unit 7 is not limited to the position information signal 14 described above. For example, the operation of the torque command unit 5 may be triggered by many events as illustrated in FIG. 3A. They may be an input that makes it possible for an operator to make a manual operation in which a determination is performed by the operator as to whether the target point is reached, a command issued by an upper-level controller 14, a command issued by a medical imaging apparatus, or the like. When the manipulator unit is pulled out of the inside of the examinee, the holding torque of the vibration-type actuator does not necessarily need to be the same as that in the operation of inserting the manipulator unit. For example, the holding torque may be maintained at the low value, and the manipulator unit may be pulled out manually by applying an external force to the manipulator unit.

In the present embodiment, the torque control command 20 is issued such that if the position information signal output from the position information detection unit 13 connected to the manipulator unit 9 or the procedure assist device 61 is received as a detection signal, then, based on this received signal, the torque control command 20 is output from the torque command unit 5 to the torque control unit 6. However, in the present embodiment, the detection unit is not limited to the unit configured to detect position information, but the detection unit may detected other control parameters.

Furthermore, the medical imaging apparatus connected to the medical manipulator according to the present embodiment is not limited to the MRI apparatus, but a large variety of medical imaging apparatuses may be employed, such as a radiographic imaging apparatus, an ultrasound imaging apparatus, or other medical imaging apparatuses capable of detecting characteristic parameters.

Next, a description is given below as to an operation based on the torque command unit 5, for example, for a case in which the attitude or the position of the medical manipulator is changed manually.

When a manipulator is used in a medical procedure, it is necessary to perform initial setting in terms of positioning of the manipulator or the like depending on a size of an examinee, an operation distance from a bed, or other factors. In the initial setting, when the torque command unit 5 receives a command from an operator, the torque command unit 5 issues a command to the pressure control unit 7 to reduce the applied pressure. As a result, the holding torque of the manipulator decreases, and it becomes possible for an operator to manually change the attitude or the position of the manipulator. After the attitude or the position of the manipulator is determined, if the operator issues a command to the torque command unit 5 to apply a pressure, the holding torque of the manipulator is increased.

In a case where a pneumatic cylinder or a pneumatic pressure control valve is employed as a pressure application mechanism, an operator may manually open the control valve to reduce the holding torque. In this case, the operator functions as the torque command unit 5.

In the example illustrated in FIG. 3B, the position information signal 14 output from the position information detection unit 13 is input to the driving circuit 12 and the torque command unit 5. Alternatively, for example, a result of a calculation performed by a calculation/control unit 130 provided in the driving circuit 12 may be output to the torque command unit 5.

By employing the above-described structure according to the first embodiment, it becomes possible to switch between a passive operation mode and an operation mode in which a high-precision position control is performed, without changing the driving circuit. This makes it possible to reduce the probability that the medical manipulator is damaged during a procedure assist action in which an inevitable movement of an examinee occurs.

Furthermore, the passivity against an external force makes it possible to manually operate the manipulator, which leads to an increase in operability in the installation or the like.

Second Embodiment

Referring to FIGS. 1D, 1E, and 1F, FIGS. 3C and 3D, and FIG. 9, the second embodiment is described below.

FIGS. 1D to 1F are block diagrams each illustrating an example of a structure of a medical manipulator including a holding torque control circuit functioning as a torque control unit according to the second embodiment. FIG. 3C is a schematic diagram illustrating a structure in which a position information detection unit 13 is connected to a manipulator unit of a medical manipulator according to the second embodiment. FIG. 3D is a block diagram illustrating details of signal flows in the structure illustrated in FIG. 3C.

First, referring to schematic diagrams illustrated in FIGS. 1D, 1E, and 1F, the second embodiment is described below. The second embodiment is different in terms of the connection from the first embodiment in that a driving circuit is configured such that a torque control unit 6 is connected to a vibrating unit 1 in the second embodiment although the torque control unit is connected to the pressure application unit in the first embodiment. The second embodiment has a feature that it is possible to reduce the holding torque by changing the driving circuit without changing the pressure application mechanism of the vibration-type actuator.

In the second embodiment, the torque control unit 6 functions as a unit that switches between a first vibration state in which the vibrating unit 1 vibrates to relatively move the moving unit 2 with respect to the vibrating unit 1 and a second vibration state in which the vibrating unit 1 vibrates so as to reduce the holding torque. The torque control unit 6 includes a holding torque control circuit 58 configured to output a driving wave to generate a particular vibration state in the vibrating unit 1 thereby reducing the holding torque of the vibration-type actuator 10. Details of the driving wave output by the holding torque control circuit 58 to generate the vibration state thereby reducing the holding torque will be described later.

In the second embodiment, the circuit configuration of the driving circuit is changed so as to be capable of changing the driving wave for exciting the vibrating unit 1 thereby switching between a mode in which the manipulator is moved to a desired position and a mode in which the manipulator moves following the movement of living body.

To provide a better understanding of the operation mechanism of the driving circuit 12 and the vibrating unit 1 according to the second embodiment, first, a description is given below as to operations of the driving circuit 12 and the driving unit 4 (vibration-type actuator) when the manipulator illustrated in FIG. 8 is driven by the vibration-type actuator illustrated in FIG. 9. In the present description, a method of driving the vibration-type actuator 10 so as to rotate by the driving torque is referred to as traveling wave driving (forward traveling wave driving or reverse traveling wave driving when a direction thereof is specified).

When the vibration-type actuator 10 illustrated in FIG. 9 is driven by a forward traveling wave or a reverse traveling wave, the driving circuit 12 illustrated in FIG. 8 applies a 2-phase AC periodic signal to two pairs of electrodes arranged on a piezo-electric element 31 of the vibrating unit 1. By varying part or all of the amplitude, the frequency, and the phase difference of the 2-phase periodic signal, it is possible to control the rotation speed and the rotation direction of the vibration-type actuator. The traveling direction of the elliptical vibration excited in the vibrating unit 1 is switched by switching the phase difference of the 2-phase periodic signal thereby switching the rotation direction of the vibration-type actuator 10. In the present embodiment, the 2-phase periodic signal refers to two or more combinations of periodic signals having phase difference information as a control parameter, wherein 0 (rad) is allowed as a value of the phase difference. Furthermore, in the present embodiment, the 2-phase periodic signal output by the driving circuit to excite the vibrating unit 1 to generate a traveling wave is referred to as a traveling wave signal (or a forward traveling wave signal or a reverse traveling wave signal when a direction thereof is specified).

An example of the holding torque control circuit 58 is a standing wave driving circuit 54 configured to output a standing wave driving signal 55 to the vibrating unit 1 as illustrated in FIG. 1E. Another example is an alternating driving circuit 56 configured to output an alternating driving signal 57 to the vibrating unit 1 as illustrated in FIG. 1F. Note that the alternating driving signal 57 is such a signal in which a forward traveling wave signal and a reverse traveling wave signal alternately appear.

Referring to FIG. 9, the operation of the vibration-type actuator 10 is described below for a case where the phase difference of the 2-phase AC periodic signal is set to be smaller than that of the traveling wave signal and the 2-phase AC periodic signal is applied to the piezoelectric element 31. In the vibrating unit 1, a traveling bending vibration is not excited but a standing wave vibration is excited. In a state in which the vibrating unit 1 has a standing wave vibration, the vibrating unit 1 provides only a force that thrusts the moving unit 2 upward, but the vibrating unit 1 does not provide a force in the rotation direction. Furthermore, in the traveling wave driving mode, the vibrating unit and the moving unit 2 are maintained in contact with each other. In contrast, in the standing wave vibration mode, the vibrating unit 1 and the moving unit 2 come into contact intermittently. Therefore, in the standing wave vibration mode, the temporal average of the frictional force acting between the vibrating unit 1 and the moving unit 2 is low. Thus, it is possible to perform the operation such that the holding torque of the driving unit is reduced while having no rotation of the vibration-type actuator 10.

Next, a modification of the standing wave driving circuit 54 is described below.

According to an embodiment, the standing wave driving circuit 54 may be configured to be capable of controlling the amplitude of the standing wave driving signal as illustrated in FIGS. 1D to 1F, thereby making it possible to control the contact area in the thrusting vibration. The method of changing the amplitude of the amplitude of the vibration excited in the vibrating unit 1 in the thrust driving is not limited to changing the amplitude of the driving signal waveform. For example, the frequency of the driving signal waveform may be changed toward or away from the natural frequency of the vibrating unit 1. That is, it is possible to change the amplitude of the vibration excited in the vibrating unit 1 by changing the frequency of the standing wave driving signal toward or away from the natural frequency of the vibrating unit 1. Alternatively, the standing wave driving circuit 54 may be configured to output the standing wave driving signal 55 such that the amplitude is set to be sufficiently small for only one of the periodic signals of the 2-phase periodic signal.

In the method of reducing the phase difference of the 2-phase periodic signal of the standing wave driving signal 55 in driving the vibrating unit 1 with the standing wave, it is not necessary to set the phase difference to zero, that is, it is not necessary that the periodic signals are in phase. There may be a phase difference in a range in which the rotation of the moving unit 2 is prevented by friction with another element or the like.

Next, referring to FIG. 9, a description is given below as to an example of a modification to the second embodiment, in which a traveling wave signal is used as the holding torque control signal 59. In the traveling wave driving, the vibrating unit 1 thrusts the moving unit 2 upward and drives moving unit 2 to move in a direction opposite to the direction of the traveling wave. However, the moving unit 2 has a very small rotational displacement that may occur each time the vibrating unit 1 is brought into contact with the moving unit 2 by the vibration wave of one period of the traveling wave signal. In the traveling wave driving, the one-period feeding operation is performed repeatedly at a high frequency in an ultrasonic range thereby causing the actuator to gain an output speed. In the present embodiment, the traveling direction of the traveling wave is alternately switched in a short time. More specifically, the phase of the traveling wave signal is switched such that forward traveling wave signals and reverse traveling wave signals appear alternately every short time within which substantially no rotation occurs on the moving unit 2. Note that in the present embodiment, a more strict definition of "substantially no rotation" of the moving unit 2 is that the rotation is limited to a small range that does not cause the manipulator to have a problem in controlling the position, and the moving unit 2 may not be completely at rest with respect to the vibrating unit 1. In the present embodiment, as described above, the signal is alternately inverted with time by switching the phase. Alternatively, another wave parameter may be changed to alternately switch between forward traveling wave signals and reverse traveling wave signals.

By changing the traveling direction of the traveling wave to alternately switch between forward traveling wave signals and reverse traveling wave signal every short time, it is possible to cancel out the rotative force acting on the moving unit 2 such that there is, macroscopically, only an upthrust force acting from the vibrating unit 1 on the moving unit 2. In this state, as with the standing wave driving, the frictional force between the vibrating unit 1 and the moving unit 2 becomes low compared with that in the state in which the vibrating unit is not vibrating or is driven by the traveling wave, and thus it is possible to control the holding torque by controlling the amplitudes of the forward and reverse traveling wave signals of the alternating signal.

Next, referring to FIG. 3C and FIG. 3D, a description is given as to a mechanism of an operation based on the torque command unit 5 in the medical manipulator with the driving circuit 12 and the position information detection unit 13 according to the second embodiment is described below. FIG. 3C is a schematic diagram illustrating a structure obtained by adding the position information detection unit 13 to the structure of the medical manipulator 30 according to the second embodiment illustrated in one of FIGS. 1D to 1F. FIG. 3D is a block diagram illustrating details of signal flows in the structure illustrated in FIG. 3C. In examples illustrated in FIG. 3C and FIG. 3D, the driving circuit 12 includes the standing wave driving circuit 54 as the torque control unit according to the second embodiment. To provide a better understanding of the operation of manipulator unit 9, the procedure assist device is not illustrated in FIG. 3C and FIG. 3D.

An example of a process is described below in which the operation mode of the medical manipulator according to the second embodiment is changed based on a command issued by the torque command unit 5. In the medical procedure assist apparatus including the procedure assist device 61, the holding torque is controlled by the torque command unit during the procedure assist action in a manner as described below. To provide a better understanding of the operation of manipulator unit 9, the procedure assist device is not illustrated in FIG. 3C and FIG. 3D.

First, a description is given below as to an operation mode employed, at a stage of inserting the manipulator unit 9 into the inside of an examinee, to precisely position the procedure assist device at a desired position in the inside of the examinee. At this stage, based on a position information signal 14 serving as a detection signal transmitted from the position information detection unit 13, the torque command unit 5 determines that a target position has not yet been reached, and thus the torque command unit 5 outputs a torque control command 20 to the driving circuit 12 to generate a particular driving torque. In accordance with the received torque control command 20, a driving signal generation unit 131 of the driving circuit 12 disables the standing wave driving circuit 54 and outputs a forward traveling wave signal to the vibrating unit 1 of the vibration-type actuator 10. As a result, a forward torque acts between the vibrating unit and the moving unit, and the manipulator unit 9 is driven the torque with respect to the supporting unit 8. Thus, as in the first embodiment, it becomes possible to move the procedure assist device until it reaches a target point.

Next, a description is given below as to an operation at a stage after the manipulator has reached the target point. It is necessary to maintain the procedure assist device in the inside of the examinee during a period in which a procedure is performed using the procedure assist device. In the present embodiment, a determination as to whether the manipulator unit 9 has reached the target position is made based on the position information signal 14 transmitted from the position information detection unit 13 to the torque command unit 5. If it is determined that the manipulator unit 9 has reached the target position, the torque command unit 5 transmits a torque control command 20 to the driving circuit 12 to reduce the holding torque. In accordance with the received torque control command 20, the driving signal generation unit 131 of the driving circuit 12 operates the standing wave driving circuit 54 to output a standing wave driving signal 55 to the vibrating unit 1 of the vibration-type actuator 10. As a result of a sequence of operations detection→position information transmission→judgment→command, the at-rest friction torque of the vibration-type actuator 10 of the driving unit 4 is reduced, and thus the holding torque of the manipulator unit 9 with respect to the supporting unit 8 is also reduced. Thus, the procedure assist device 61 and the manipulator unit 9 inserted in the inside of the examinee are not fixed with respect to the on-apparatus reference but they move following the movement of the examinee 40. As described above, in the present embodiment, the medical manipulator operates according to the position information of the manipulator such that the manipulator is prevented from being damaged.

Next, an operation mode of the manipulator after the end of the procedure period is described below. To pull the procedure assist device out of the examinee 40, the torque command unit 5 issues a torque control command 20 to the driving circuit 12 to generate a driving torque. This makes it possible for the manipulator, as in the inserting operation, to pull the procedure assist device out of the inside of the examinee 40 while maintaining a particular holding torque.

As in the first embodiment, a trigger that causes the torque command unit 5 to issue a command to the driving apparatus 12 is not limited to the position information signal 14 described above. For example, the operation of the torque command unit 5 may be triggered by many events as illustrated in FIG. 3C. They may be a manual operation command in which a determination is performed by an operator as to whether the target point is reached, a command issued by an upper-level controller 14, a command issued by a medical imaging apparatus, or the like. As for the operation of pulling the manipulator unit out of the inside of the examinee, the holding torque of the vibration-type actuator does not necessarily need to be the same as that in the operation of inserting the manipulator unit. For example, the holding torque may be maintained at the low value, and the manipulator unit may be pulled out manually by applying an external force to the manipulator unit.

When the medical manipulator is used in the procedure assist action or the like, an inevitable movement of an examinee occurs. Therefore, also in the second embodiment, as described above, the holding torque is reduced in response to the movement of an examinee such that the procedure assist device and the manipulator unit are allowed to move following the movement of the examinee. This makes it possible to reduce the probability that the medical manipulator is damaged during the procedure assist action.

Also in the second embodiment, as in the first embodiment, the torque command unit 5 may be connected so as to receive an upper-level command issued by an operator or the like as illustrated in FIG. 3C to control the holding torque of the vibration-type actuator thereby making it possible to reduce the holding torque of the medical manipulator in correct timing according to the intention of the operator. Furthermore, the torque command unit 5 may be configured to receive an upper-level command issued by an operator to continuously or stepwisely specify a holding torque, thereby making it possible to adjust the holding force according to the intention of the operator. An input unit for use by an operator to input the upper-level command 5 may be disposed on the manipulator unit such that the operator is allowed to more easily operate the medical manipulator in terms of procedure assist action, positioning in installation, or the like.

As described above, in the present embodiment, the medical manipulator is capable of switching between a passive operation mode and an operation mode in which a high-precision position control is performed, without changing the structure of the vibration-type actuator. This makes it possible to reduce the probability that the medical manipulator is damaged even during a procedure assist action in which an inevitable movement of an examinee occurs. Furthermore, it is possible to achieve an increase in operability in the installation or the like.

Examples of modifications of the medical manipulator that may be possible for both the first and second embodiments are described below.

Other Embodiments

Referring to FIG. 2A and FIG. 2B, a description is given below as to examples of medical procedure assist apparatuses realized by connecting a procedure assist device 61 to a medical manipulator according to an embodiment.

In the example illustrated in FIG. 2A, a puncture unit 15 that is to be put into the inside of an examinee is connected in a relatively movable manner to the manipulator unit 9 thereby realizing a medical procedure assist apparatus functioning as a medical puncture apparatus. One end of the puncture unit 15 is fixed to a puncture unit driving unit 16 which is fixed to the manipulator unit 9. More specifically, the connection is made such that it is possible to control the relative position of the puncture unit 15 with respect to the manipulator unit 9 and it is also possible to control the relative position of the puncture unit 15 with respective to the supporting unit 8. By forming the medical manipulator 30 in the above-described manner, it becomes possible to more safely assist a puncture procedure operation.

In the example illustrated in FIG. 2B, instead of the puncture unit 15 and the puncture unit driving unit 16 illustrated in FIG. 2A, an extraction unit 17 configured to extract a body tissue of an examinee and an extraction unit driving unit 18 are disposed thereby realizing a biopsy apparatus. By forming the medical manipulator 30 in the above-described manner according to the embodiment, it becomes possible to more safely assist an extraction operation.

Note that in FIG. 2A and FIG. 2B, to provide a better understanding of the connection between the procedure assist device 61 and the medical manipulator 30 according to the embodiment, the torque control unit is not illustrated.

As described above, by connecting an operation assist tool such as a surgical knife, a forceps, or the like, a test assist tool, a procedure assist device such as a sensor or the like to the manipulator unit of the medical manipulator according to one of the embodiments, it is possible to realize the medical manipulator having high functionality.

Next, referring to FIGS. 7A and 7B, the supporting unit 8 is described below. FIGS. 7A and 7B illustrate relative locations of an examinee and a medical manipulator according to one of the embodiment, and also illustrate a manner in which a bed is connected to the medical manipulator. The positioning of the supporting unit 8 with respect to the examinee may be performed with reference to the surface of the examinee or equipment fixed to the examinee, a tool placed on clothes, a part of an external apparatus such as a bed, or the like. In the example illustrated in FIGS. 7A and 7B, the supporting unit 8 is fixed to the bed 41.

The supporting unit 8 may be formed so as to has a rigid structure to ensure that the driving unit 4 and the manipulator unit 9 are stably supported even when the medical manipulator in operation. To achieve proper degrees of freedom on the positioning of the driving unit 4 with respect to the supporting unit 8, the supporting unit 8 may have an adjustment mechanism that allows it to adjusts the position and the direction of the rotation, the linear movement, the curved movement, or the like. In the example illustrated in FIGS. 7A and 7B, the supporting unit 8 has an adjustment mechanism that allows it to make a vertical position adjustment a horizontal position adjustment, an azimuth adjustment, and an elevation angle adjustment. The adjustment mechanism may further include a driving source that allows it to remotely make the positioning.

FIG. 4A illustrates an example of a structure in which a plurality of vibration-type actuators are serially connected to achieve a multiple-joint mechanism. In the example illustrated in FIG. 4A, four degrees of freedom are achieved corresponding to a procedure assist device driving unit 65 configured to drive a procedure assist device 61 in a desired moving direction, a driving unit 4 configured to drive a manipulator unit 9 in a uniaxial direction, a rotation driving unit 48 configured to control an angle phi2 with respect to an intermediate manipulator unit 28 of the manipulator unit 9, and a rotation driving unit 49 configured to control an angle phi1 with respect to a supporting unit 8 of the intermediate manipulator unit 28, thereby achieving four degrees of freedom. In the case where the medical manipulator according to an embodiment has two or more degrees of freedom, the vibration-type actuator may control all degrees of freedom, or the vibration-type actuator may control part of degrees of freedom and the remaining degrees of freedom may be controlled manually or other actuators.

Referring to FIG. 4B, a description is given below as to a structure in which a plurality of vibration-type actuators, such as those illustrated in FIG. 4A, function as driving elements of respective degrees of freedom. FIG. 4B illustrates a manner in which a plurality of vibration-type actuators are assigned to respective degrees of freedom according to the second embodiment. In this example, the plurality of vibration-type actuators are disposed in the driving unit 4 although they are not illustrated in FIG. 4B. Each of the constituent elements 401, 402, 403, and 404 corresponds to the driving circuit 12 illustrated in FIG. 3C.

In the present embodiment, the torque command unit 5 may issue separate holding torque commands to the constituent elements 401, 402, 403, and 404 associated with the respective degrees of freedom, or the torque command unit 5 may issue a holding torque command to control all degrees of freedom. In the case where the holding torques associated with the constituent elements of the respective degrees of freedom are separately controlled, for example, a holding torque for a degree of freedom of an axis parallel to a direction A may be set to be fixed to a high value while a holding torque for a degree of freedom of an axis parallel to a direction B may be set to be low such that passivity is obtained only in the direction B. The direction A may be a direction in which the manipulator is inserted, and the direction B may be a direction perpendicular to the direction in which the manipulator is inserted.

Next, referring to FIG. 5, a description is given below as to an example of a manner in which the medical manipulator according to the present embodiment is connected to an external apparatus. In the example illustrated in FIG. 5, an MRI apparatus is connected as an external apparatus 27 to the driving circuit 12 according to the present embodiment. The driving circuit 12 includes a torque command unit 5 that is connected to an upper-level command transmission unit 45 of the external apparatus 27. When the upper-level command transmission unit 45 detects a change in a characteristic parameter, position information, or the like monitored by the external apparatus 27, or when the upper-level command transmission unit 45 detects a command manually issued by an operator, an examinee, or the like, the upper-level command transmission unit 45 transmits an upper-level command 67 to the torque command unit 5. The external apparatus 27 may also include a transmission unit 24 configured to transmit a target position signal 26 based on target position information stored in the external apparatus 27 to a target position signal receiving unit 25 disposed in the driving circuit 12. In this structure, the driving circuit 12 may compare the position information of the manipulator unit 9 with the target position of the manipulator unit 9, transmit a forward traveling wave signal or a reverse traveling wave signal as the manipulator unit driving signal 22, and, as required, transmit a standing wave driving signal or an alternating driving signal as the holding torque control signal 59.

Next, referring to FIGS. 7A to 7D, a description is given below as to a manner in which the medical manipulator according to the present embodiment is connected to an examinee or a medical imaging apparatus. FIG. 7A and FIG. 7B are schematic diagrams illustrating a medical imaging system viewed from longitudinal and laterals sides of a movable bed. The medical imaging system includes the medical manipulator according to the present embodiment connected to the movable bed including a bed base 42 and a bed 41. In the structures illustrated in FIGS. 7A to 7D, the examinee 40 may be placed firmly on a bed with a positioning unit such as a belt, a cushioning unit, or the like (not illustrated). Therefore, by fixing the supporting unit 8 to the bed, the supporting unit 8 is substantially positioned with respect to the examinee 40. FIG. 7C and FIG. 7D are schematic diagrams illustrating a system in which the medical manipulator according to the present embodiment is applied to the medical imaging apparatus with the movable bed illustrated in FIGS. 7A and 7B.

A work distance, a size, and other factors of the medical manipulator according to the present embodiment are set such that the existence of the medical manipulator does not disturb the image capturing operation by the medical imaging apparatus. In the example illustrated in FIGS. 7C and 7D, the medical manipulator according to the present embodiment is connected to the bed 41 such that the medical manipulator and the bed 41 are allowed to be put into a cylinder-shape measurement unit 44 of a MRI apparatus 43.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135453, filed Jun. 15, 2012, which is hereby incorporated by reference herein in its entirety.

The invention claimed is:

1. A medical manipulator comprising:
a driving unit including a vibration-type actuator including a vibrating unit configured to generate a vibration wave in response to being excited by an applied AC voltage, a moving unit configured to relatively move with respect to the vibrating unit in response to a reception of the vibration wave, and a pressure application unit configured to apply a pressure between the vibrating unit and the moving unit;
a manipulator unit connected to the driving unit and configured to be movable by being driven by the driving unit;
a supporting unit configured to support the driving unit and the manipulator unit;
a driving circuit connected to the vibrating unit and configured to apply an AC voltage to the vibrating unit; and
a torque control unit configured to control a holding torque with which the moving unit is held by the vibrating unit.

2. The medical manipulator according to claim 1, wherein the supporting unit supports the driving unit by supporting one of the vibrating unit and the moving unit, and the manipulator unit is supported by the other one of the vibrating unit and the moving unit.

3. The medical manipulator according to claim 1, further comprising a torque command unit connected to the torque control unit and configured to output a torque control command to the torque control unit to control the holding torque.

4. The medical manipulator according to claim 1, wherein the torque control unit is a pressure control unit connected to the pressure application unit and configured to control the pressure.

5. The medical manipulator according to claim 4, wherein the pressure application unit is a gas pressure cylinder or a hydraulic cylinder, and the pressure control unit is a control valve configured to control a flow rate of a compressed gas or an incompressible liquid.

6. The medical manipulator according to claim 5, wherein the gas pressure cylinder is a pneumatic cylinder configured to be controlled by a compressed air, and the pressure control unit is an electromagnetic valve configured to control the flow rate of the compressed air.

7. The medical manipulator according to claim 4, wherein the pressure application unit includes an electromagnet and an elastic element, and the pressure control unit is an electromagnet control circuit configured to control a magnitude of a current supplied to the electromagnet.

8. The medical manipulator according to claim 1, wherein the torque control unit is holding torque control circuit disposed in the driving circuit and configured to output a holding torque control signal to the vibrating unit.

9. The medical manipulator according to claim 8, wherein the holding torque control circuit is a standing wave driving circuit configured to output, to the vibrating unit, the holding torque control signal including a standing wave driving signal to excite a standing wave in the vibrating unit.

10. The medical manipulator according to claim 8, wherein the holding torque control circuit is an alternating driving circuit configured to output, to the vibrating unit, the holding torque control signal including an alternating driving signal in which a forward traveling wave signal and a reverse traveling wave signal appear alternately.

11. The medical manipulator according to claim 1, wherein the medical manipulator includes a plurality of driving units, at least two of which are disposed at locations on a path from the supporting unit to the manipulator unit such that the respective driving units are allowed to drive the manipulator unit in different directions.

12. The medical manipulator according to claim 11, wherein the torque control unit is a unit configured to control at least one of the plurality of driving unit to reduce the holding torque based on the received torque control command.

13. The medical manipulator according to claim 1, wherein the supporting unit includes a gravitational force compensation unit.

14. The medical manipulator according to claim 13, wherein the gravitational force compensation unit is a counterweight disposed at a location opposing the manipulator unit via the driving unit and connected to the supporting unit.

15. A medical procedure assist apparatus comprising:
the medical manipulator including a driving unit including a vibration-type actuator including a vibrating unit configured to generate a vibration wave in response to being excited by an applied AC voltage, a moving unit configured to relatively move with respect to the vibrating unit in response to a reception of the vibration wave, and a pressure application unit configured to apply a pressure between the vibrating unit and the moving unit; a manipulator unit connected to the driving unit and configured to be movable by being driven by the driving unit; a supporting unit configured to support the driving unit and the manipulator unit; a driving circuit connected to the vibrating unit and configured to apply an AC voltage to the vibrating unit; and a torque control unit configured to control a holding torque with which the moving unit is held by the vibrating unit; and a procedure assist device connected to the manipulator unit and configured to assist a procedure action.

16. The medical procedure assist apparatus according to claim 15, wherein the procedure assist device is a puncture unit to be put into the inside of an examinee or an extraction unit configured to extract a body issue of the examinee.

17. The medical manipulator according to claim 3, wherein the torque control command is output by the torque command unit to the torque control unit based on a manual operation command issued by an operator or examinee to the torque command unit.

18. The medical manipulator according to claim 3, wherein the torque control command is output by the torque command unit to the torque control unit based on a detection signal output from a detection unit connected to the manipulator unit or the procedure assist device.

19. A medical imaging system comprising:
the medical manipulator including a driving unit including a vibration-type actuator including a vibrating unit configured to generate a vibration wave in response to being excited by an applied AC voltage, a moving unit configured to relatively move with respect to the vibrating unit in response to a reception of the vibration wave, and a pressure application unit configured to apply a pressure between the vibrating unit and the moving unit; a manipulator unit connected to the driving unit and configured to be movable by being driven by the driving unit; a supporting unit configured to support the driving unit and the manipulator unit; a driving circuit connected to the vibrating unit and configured to apply an AC voltage to the vibrating unit; and a torque control unit configured to control a holding torque with which the moving unit is held by the vibrating unit; and
a medical imaging apparatus including a transmission unit configured to transmit position information associated with a target position,
the driving circuit including a target position signal receiving unit configured to receive the position information associated with the target position.

20. The medical imaging system according to claim 19, wherein the medical imaging apparatus includes one of an MRI apparatus, a radiographic imaging apparatus, and an ultrasound imaging apparatus.

* * * * *